United States Patent
Savoy et al.

(10) Patent No.: US 10,386,351 B2
(45) Date of Patent: Aug. 20, 2019

(54) METHODS FOR DETECTING AND QUANTIFYING ANALYTES USING GAS SPECIES DIFFUSION

(71) Applicant: Nanohmics, Inc., Austin, TX (US)

(72) Inventors: Steve M. Savoy, Austin, TX (US);
Kyle W. Hoover, Austin, TX (US);
Daniel R. Mitchell, Austin, TX (US);
Jeremy J. John, Austin, TX (US);
Chris W. Mann, Austin, TX (US);
Alexander P. Greis, Austin, TX (US)

(73) Assignee: NANOHMICS, INC., Austin, TX (US)

( * ) Notice: Subject to any disclaimer, the term of this patent is extended or adjusted under 35 U.S.C. 154(b) by 0 days.

(21) Appl. No.: 15/372,248

(22) Filed: Dec. 7, 2016

(65) Prior Publication Data
US 2017/0160250 A1    Jun. 8, 2017
US 2017/0363600 A9    Dec. 21, 2017

Related U.S. Application Data

(60) Provisional application No. 62/263,769, filed on Dec. 7, 2015.

(51) Int. Cl.
*G01N 33/00* (2006.01)
*G01N 27/12* (2006.01)

(52) U.S. Cl.
CPC ....... *G01N 33/0036* (2013.01); *G01N 27/125* (2013.01)

(58) Field of Classification Search
CPC .......................... G01N 33/0036; G01N 27/125
See application file for complete search history.

(56) References Cited

U.S. PATENT DOCUMENTS

| | | | |
|---|---|---|---|
| 3,695,848 A | 10/1972 | Taguchi | |
| 3,971,065 A | 7/1976 | Bayer | |
| 4,542,640 A | 9/1985 | Clifford | |
| 5,045,285 A | 9/1991 | Kolesar, Jr. | |
| 5,077,210 A | 12/1991 | Eigler et al. | |

(Continued)

FOREIGN PATENT DOCUMENTS

| | | |
|---|---|---|
| EP | 0652436 B1 | 3/2002 |
| WO | 0032044 A1 | 6/2000 |

(Continued)

OTHER PUBLICATIONS

Pevzner et al., "Knocking down highly-ordered large-scale nanowire arrays", Nano Lett. vol. 10, pp. 1202-1208, (2010).

(Continued)

*Primary Examiner* — Melanie Brown
(74) *Attorney, Agent, or Firm* — Murphy Strategic IP; George L. Murphy

(57) ABSTRACT

Methods and sensors for detection and quantification of one or more analyte in a test sample are described. A response profile of a gas sensor to a control sample of a known interrogator gas is determined. The gas sensor is exposed to a test sample then to a second sample comprising the known interrogator gas, and a test sample response profile of the gas sensor is determined. One or more test sample sensor response profiles are compared with one or more control sensor response profiles for detecting, identifying, and quantifying one or more analytes in the test sample.

17 Claims, 14 Drawing Sheets

(56) References Cited

U.S. PATENT DOCUMENTS

| | | |
|---|---|---|
| 5,106,756 A | 4/1992 | Zaromb |
| 5,284,570 A * | 2/1994 | Savage .............. A61B 5/14539 |
| | | 204/403.02 |
| 5,411,709 A | 5/1995 | Furuki et al. |
| 5,694,932 A | 12/1997 | Michel |
| 5,807,701 A | 9/1998 | Payne et al. |
| 5,837,832 A | 11/1998 | Chee et al. |
| 5,889,196 A | 3/1999 | Ueno et al. |
| 5,936,730 A | 8/1999 | Foley et al. |
| 6,010,616 A | 1/2000 | Lewis et al. |
| 6,028,331 A | 2/2000 | Mastromatteo et al. |
| 6,238,869 B1 | 5/2001 | Kris et al. |
| 6,268,222 B1 | 7/2001 | Chandler et al. |
| 6,277,489 B1 | 8/2001 | Abbott et al. |
| 6,287,452 B1 | 9/2001 | Allen et al. |
| 6,327,410 B1 | 12/2001 | Walt et al. |
| 6,391,562 B2 | 5/2002 | Kambara et al. |
| 6,426,184 B1 | 7/2002 | Gao et al. |
| 6,432,360 B1 | 8/2002 | Church |
| 6,468,657 B1 | 10/2002 | Hou et al. |
| 6,479,297 B1 | 11/2002 | Sandhu |
| 6,567,163 B1 | 5/2003 | Sandstrom |
| 6,638,416 B2 | 10/2003 | Wang et al. |
| 6,649,403 B1 | 11/2003 | McDevitt et al. |
| 6,677,606 B1 | 1/2004 | Rajh et al. |
| 6,689,321 B2 | 2/2004 | Sandhu |
| 6,787,308 B2 | 9/2004 | Balasubramanian et al. |
| 6,833,601 B2 | 12/2004 | Murakami |
| 6,849,166 B2 | 2/2005 | Kita |
| 6,849,239 B2 | 2/2005 | Morris |
| 6,872,645 B2 | 3/2005 | Duan et al. |
| 7,057,168 B2 | 6/2006 | Miller et al. |
| 7,118,900 B2 | 10/2006 | Seul et al. |
| 7,129,554 B2 | 10/2006 | Lieber et al. |
| 7,182,916 B2 | 2/2007 | Noda et al. |
| 7,211,654 B2 | 5/2007 | Gao et al. |
| 7,297,497 B2 | 11/2007 | Montagu et al. |
| 7,301,199 B2 | 11/2007 | Lieber et al. |
| 7,312,095 B1 | 12/2007 | Gabriel et al. |
| 7,321,143 B2 | 1/2008 | Kunath et al. |
| 7,335,153 B2 | 2/2008 | Seul et al. |
| 7,335,942 B2 | 2/2008 | Edinger et al. |
| 7,348,184 B2 | 3/2008 | Rich et al. |
| 7,385,267 B2 | 6/2008 | Lieber et al. |
| 7,449,757 B2 | 11/2008 | Bradley et al. |
| 7,460,958 B2 | 12/2008 | Walsh et al. |
| 7,489,017 B2 | 2/2009 | Patel et al. |
| 7,491,680 B2 | 2/2009 | Gao et al. |
| 7,544,638 B2 | 6/2009 | Gao et al. |
| 7,553,958 B2 | 6/2009 | Gao et al. |
| 7,575,933 B2 | 8/2009 | Gabriel et al. |
| 7,786,530 B2 | 8/2010 | Kakoschke et al. |
| 7,838,466 B2 | 11/2010 | Gao et al. |
| 7,859,029 B2 | 12/2010 | Lee et al. |
| 7,948,041 B2 | 5/2011 | Bryant et al. |
| 8,443,647 B1 | 5/2013 | Kolmakov et al. |
| 8,450,131 B2 | 5/2013 | Savoy et al. |
| 8,754,454 B2 | 6/2014 | Bryant et al. |
| 8,900,517 B2 | 12/2014 | Gabriel et al. |
| 9,063,053 B2 | 6/2015 | Patolsky et al. |
| 9,603,560 B2 | 3/2017 | Monty et al. |
| 9,768,162 B2 | 9/2017 | Savoy et al. |
| 9,828,696 B2 | 11/2017 | Savoy et al. |
| 2001/0029049 A1 | 10/2001 | Walt et al. |
| 2002/0018199 A1 | 2/2002 | Blumenfeld et al. |
| 2002/0028455 A1 | 3/2002 | Laibinis et al. |
| 2002/0146745 A1 | 10/2002 | Natan et al. |
| 2003/0040129 A1 | 2/2003 | Shah |
| 2003/0065452 A1 * | 4/2003 | Hickman .............. B82Y 30/00 |
| | | 702/19 |
| 2003/0118595 A1 | 6/2003 | Niemeyer et al. |
| 2004/0121339 A1 | 6/2004 | Zhou et al. |
| 2004/0132070 A1 | 7/2004 | Star et al. |
| 2004/0136866 A1 | 7/2004 | Pontis et al. |
| 2004/0161370 A1 | 8/2004 | Sunshine et al. |
| 2004/0248144 A1 | 12/2004 | Mir |
| 2005/0032060 A1 | 2/2005 | Shah et al. |
| 2005/0053949 A1 | 3/2005 | Silin |
| 2005/0065446 A1 | 3/2005 | Talton |
| 2005/0095649 A1 | 5/2005 | Aebersold et al. |
| 2005/0130174 A1 | 6/2005 | Yijia et al. |
| 2005/0142567 A1 | 6/2005 | Su et al. |
| 2006/0035229 A1 | 2/2006 | Schwarnweber et al. |
| 2006/0068504 A1 | 3/2006 | Kogi |
| 2006/0137669 A1 | 6/2006 | Lindner |
| 2006/0263763 A1 | 11/2006 | Simpson et al. |
| 2007/0015213 A1 | 1/2007 | Mutz et al. |
| 2007/0048180 A1 | 3/2007 | Gabriel et al. |
| 2007/0138007 A1 | 6/2007 | Yemini et al. |
| 2007/0158547 A1 | 7/2007 | Rich et al. |
| 2007/0224616 A1 | 9/2007 | Gulari et al. |
| 2008/0044925 A1 | 2/2008 | Isojima et al. |
| 2008/0146459 A1 | 6/2008 | Iwakura et al. |
| 2008/0221806 A1* | 9/2008 | Bryant .................. G01N 27/127 |
| | | 702/22 |
| 2008/0293591 A1 | 11/2008 | Taussig et al. |
| 2008/0312105 A1 | 12/2008 | Bacher et al. |
| 2009/0018027 A1 | 1/2009 | Ronald et al. |
| 2009/0036324 A1 | 2/2009 | Fan et al. |
| 2009/0117571 A1* | 5/2009 | Solanki .............. G01N 33/5438 |
| | | 435/6.11 |
| 2009/0153864 A1 | 6/2009 | Kim et al. |
| 2009/0156427 A1 | 6/2009 | Zhang et al. |
| 2009/0211437 A1 | 8/2009 | Fleischer et al. |
| 2011/0071037 A1 | 3/2011 | Muller et al. |
| 2011/0179852 A1 | 7/2011 | Polonsky et al. |
| 2012/0178199 A1* | 7/2012 | Savoy .................. G01N 27/4148 |
| | | 438/49 |
| 2012/0245055 A1 | 9/2012 | Savoy et al. |
| 2012/0263922 A1 | 10/2012 | Advincula |
| 2014/0212979 A1 | 7/2014 | Burgi et al. |
| 2014/0249052 A1 | 9/2014 | Mehmet et al. |
| 2014/0332407 A1* | 11/2014 | Mai .................... G01N 27/3276 |
| | | 205/777.5 |
| 2017/0160221 A1 | 6/2017 | Savoy et al. |
| 2017/0160227 A1 | 6/2017 | Savoy et al. |
| 2017/0343538 A9 | 11/2017 | Savoy et al. |

FOREIGN PATENT DOCUMENTS

| | | |
|---|---|---|
| WO | 0079243 A1 | 12/2000 |
| WO | 0100876 A1 | 1/2001 |
| WO | 2001000876 A1 | 1/2001 |
| WO | 2002103371 A2 | 12/2002 |
| WO | 2003079401 A2 | 9/2003 |
| WO | 2003095469 A1 | 11/2003 |
| WO | 2003102546 A2 | 12/2003 |
| WO | 2004011672 A1 | 5/2004 |
| WO | 2005030978 A2 | 4/2005 |
| WO | 2005103718 A1 | 11/2005 |
| WO | 20050103718 A1 | 11/2005 |
| WO | 2006113618 A1 | 10/2006 |
| WO | 2006124089 A1 | 11/2006 |
| WO | 2007/082955 * | 7/2007 |
| WO | 2007139849 A2 | 12/2007 |
| WO | 2008027571 A2 | 3/2008 |
| WO | 2008033848 A2 | 3/2008 |
| WO | 2008082713 A2 | 7/2008 |
| WO | 2010135834 A1 | 12/2010 |
| WO | 2012078908 A1 | 6/2012 |
| WO | 2012151306 A2 | 11/2012 |
| WO | 2013008170 A2 | 1/2013 |

OTHER PUBLICATIONS

Stern et al., "Semiconductin nanowire field-effect transistor biomolecular sensors", IEEE Trans. Electron Devices, vol. 55, No. 11, pp. 3119-3130, (2008).

Comini et al., "Metal oxide nanowires as chemical sensors", Materials Today, vol. 13, No. 7-8, pp. 36-44 (2010).

Liu et al, "A Survey on Gas Sensing Technology", Sensors, vol. 12, pp. 9635-9665, (Jul. 16, 2012).

(56) References Cited

OTHER PUBLICATIONS

Fine et al, "Metal Oxide Semi-Conductor Gas Sensors in Environmental Monitoring", Sensors, vol. 10, pp. 5469-5502, (Jun. 1, 2010).

Gao et al, "Light directed massively parallel on-chip synthesis of peptide arrays with t-Boc chemistry", Proteomics, vol. 3, pp. 2135-2141, (2003).

Yoon, "Current Trends in Sensors Based on Conducting Polymer Nanomaterials", Nanomaterials, vol. 2013 (3), pp. 524-529.

Ju et al, "Single-carbon discrimination by selected peptides for individual detection of volatile organic compounds", Scientific Reports, vol. 5, Article No. 9196, pp. 1-6, (Mar. 17, 2015).

Arrieta A et al, "Voltammetric sensor array based on conducting polymer-modified electrodes for the discrimination of liquids" vol. 49, No. 26, pp. 4543-4551, Oct. 15, 2004.

Ghanashyam Acharya et al, "Rapid Detection of S-Adenosyl Homocysteine Using Self-Assembled Optical Diffraction Gratings" vol. 47, No. 6, pp. 1051-1053, Jan. 25, 2008.

Pouthas F et al, "DNA detection on transistor arrays following mutation-specific enzymatic amplification", vol. 84, No. 9, pp. 1594-1596, Mar. 1, 2004.

Arjang Hassibi et al, "A Programmable 0.18-CMOS Electrochemical Sensor Microarray for Biomolecular Detection", vol. 6, No. 6, pp. 1380-1388, Dec. 1, 2006.

Kodoyianni, "Label-free analysis of biomolecular interactions using SPR imaging", Biotechniques vol. 50:(1), pp. 32-40, 2011.

Mohd Azmi et al., "Highly sensitive covalently functionalised integrated silicon nanowire biosensor devices for detection of cancer risk biomarker", Biosensors and Bioelectronics, vol. 52, pp. 216-224, (Sep. 3, 2013).

Lichtenstein et al, "Supersensitive fingerprinting of explosives by chemically modified nanosensors arrays", Nature Communications., vol. 5, pp. 4195-4207, (Jun. 24, 2014).

Xiao et al, "Label-Free Electronic Detection of Thrombin in Blood Serum by Using an Aptamer-Based Sensor", Angew. Chem. Int. Ed., vol. 44, pp. 5456-5459, (2005).

PCT International Searching Authority; International Search Report and Written Opinion of the International Searching Authority issued in PCT Application PCT/US2012/030133, dated Jul. 18, 2012, pp. 1-14.

Office Action issued in U.S. Appl. No. 13/070,077, dated Jun. 5, 2012.

Office Action issued in U.S. Appl. No. 13/070,077, dated Aug. 7, 2012.

Office Action issued in U.S. Appl. No. 13/070,077, dated Dec. 26, 2012.

Office Action issued in U.S. Appl. No. 13/070,077, dated Feb. 7, 2013.

Office Action issued in U.S. Appl. No. 13/070,077, dated Apr. 4, 2013.

Office Action issued in U.S. Appl. No. 13/070,077, dated Apr. 23, 2014.

Office Action issued in U.S. Appl. No. 13/070,077, dated Nov. 6, 2014.

Office Action issued in U.S. Appl. No. 13/070,077, dated Mar. 19, 2015.

Office Action issued in U.S. Appl. No. 13/070,077, dated Oct. 20, 2015.

Office Action issued in U.S. Appl. No. 13/070,077, dated May 12, 2017.

Office Action issued in U.S. Appl. No. 13/070,077, dated Jul. 24, 2017.

Samain et al, "Differentiating a Diverse Range of Volatile Organic Compounds with Polyfluorophore Sensors Built on a DNA Scaffold", Chem. Eur. J., vol. 17, pp. 174-183, (Dec. 10, 2010).

Thewes et al, "A CMOS Medium Density DNA Microarray with Electronic Readout", Mater. Res. Soc. Symp. Proc., vol. 869, pp. D3.4.1-D3.4.11, (2005).

Stadler et al, "Multifunctional CMOS Microchip Coatings for Protein and Peptide Arrays", J. Proteome Res., vol. 6, pp. 3197-3202, (Jul. 27, 2007).

Rodrigues et al, "Coating of Solid-Phase Microextraction Fibers with Chemically Bonded Silica Particles: Selective Extraction of Polycyclic Aromatic Hydrocarbons from Drinking Water Samples", J. Chromat. Sci., vol. 40, pp. 489-494, (2002).

Schroder et al, "Addressable Microfluidic Polymer Chip for DNA-Directed Immobilization of Oligonucleotide-Tagged Compounds", Small Jour., vol. 5(13), pp. 1547-1552, (Mar. 26, 2009).

Platt et al, "Aptamer evolution for array-based diagnostics", Anal. Biochem., vol. 390, pp. 203-205, (Apr. 15, 2009).

Pizzoni et al, "Selection of peptide ligands for piezoelectric peptide based gas sensors arrays using a virtual screening approach", Biosensors Bioelectronics, vol. 52, pp. 247-254, (Sep. 4, 2013).

Niemeyer et al, "Combination of DNA-directed immobilization and immuno-PCR: very sensitive antigen detection by means of self-assembled DNA±protein conjugates", Nucl. Acids Res., vol. 31(16), pp, e90, (2003).

McNally et al, Self-assembly of micro- and nano-scale particles using bio-inspired events, Appl. Surf. Sci., vol. 214, pp. 109-119, (2003).

McCauley et al, "Aptamer-based biosensor arrays for detection and quantification of biological macromolecules" Anal. Biochem., vol. 319, pp. 244-250, (2003).

Kozak et al, "Improving the Signal-to-Noise Performance of Molecular Diagnostics with PEG-Lysine Copolymer Dendrons", Biomacromolecules, vol. 10, pp. 360-365, (Jan. 21, 2009).

Li et al, "In2O3 nanowires as chemical sensors", Applied Phys. Letters, vol. 82(10), pp. 1613-1615, (Mar. 10, 2003).

Kong et al, "Nanotube Molecular Wires as Chemical Sensors", Science, vol. 287, pp. 622-625, (Jan. 28, 2000).

Ivanov et al, "Antibodies Immobilized as Arrays to Profile Protein Post-translational Modifications in Mammalian Cells", Molec. Cell. Proteomics, vol. 3.8, pp. 788-795, (May 3, 2004).

Hui, "Guided molecular self-assembly: a review of recent efforts", Smart Mater. Struct., vol. 12, pp. 264-271, (Mar. 27, 2003).

Hatchett et al, "Composites of Intrinsically Conducting Polymers as Sensing Nanomaterials", B Chem. Rev., pp. A-U, (Jan. 3, 2008).

Dandy et al, "Array feature size influences nucleic acid surface capture in DNA microarrays", Proc. Natl. Acad. Sci., vol. 104(20), pp. 8223-8228, (May 15, 2007).

Compagnone et al, "Gold nanoparticles-peptide based gas sensor arrays for the detection of food aromas", Biosensors Bioelectronics, vol. 42, pp. 618-625, (Nov. 22, 2012).

Chhabra et al, "Spatially Addressable Multiprotein Nanoarrays Templated by Aptamer-Tagged DNA Nanoarchitectures", J. Am. Chem. Soc., vol. 129, pp. 10304-10305, (2007).

Bashir, "DNA Nanobiostructures", Materials Today, vol. Nov.-Dec. 2001, pp. 30-39, (2001).

Park et al, "Array-Based Electrical Detection of DNA with Nanoparticle Probes", Science, vol. 295, pp. 1503-1506, (Feb. 22, 2002).

Cao et al, "Silicon Nanowire-Based Devices for Gas-Phase Sensing", Sensors, vol. 14, pp. 245-271, (Dec. 24, 2013).

De Smet et al, "Organic Surface Modification of Silicon Nanowire-Based Sensor Devices", in Nanowires—Implementations and Applications, Dr. Abbass Hashim (Ed.), InTech, Rijeka, Croatia, Ch. 13, pp. 267-288, (Jul. 18, 2011).

Edelstein et al, "The BARC biosensor applied to the detection of biological warfare agents", Biosensors & Bioelectronics, vol. 14, pp. 805-813, (2000).

Galoppini, "Linkers for anchoring sensitizers to semiconductor nanoparticles", Coordination Chemistry Reviews, vol. 248, pp. 1283-1297, (May 28, 2004).

Georgiev et al, "Fully CMOS-compatible top-down fabrication of sub-50 nm silicon nanowire sensing devices", Microelectronic Engineering, vol. 118, pp. 47-53, (Jan. 7, 2014).

Huang et al, "Gas Sensors Based on Semiconducting Metal Oxide One-Dimensional Nanostructures", Sensors, vol. 9, pp. 9903-9924, (Dec. 4, 2009).

Kanan et al, "Semiconducting Metal Oxide Based Sensors for Selective Gas Pollutant Detection", Sensors, vol. 9, pp. 8158-8196, (Oct. 16, 2009).

(56) References Cited

OTHER PUBLICATIONS

Kim et al, "Advances and new directions in gas-sensing devices", Acta Materialia, vol. 61, pp. 974-1000, (2013).

Kim et al, "Direct label-free electrical immunodetection in human serum using a flow-through-apparatus approach with integrated field-effect transistors", Biosensors and Bioelectronics, vol. 25, pp. 1767-1773, (Dec. 29, 2009).

Korotcenkov et al, "Engineering approaches for the improvement of conductometric gas sensor parameters Part 1. Improvement of sensor sensitivity and selectivity (short survey)", Sensors and Actuators B:Chemical, vol. 188, pp. 709-728, (Aug. 7, 2013).

Lund et al, "Label-Free Direct Electronic Detection of Biomolecules with Amorphous Silicon Nanostructures", Nanomedicine, vol. 2(4), pp. 230-238, (Dec. 2006).

McAlpine et al, "Peptide-Nanowire Hybrid Materials for Selective Sensing of Small Molecules", J Am Chem Soc, vol. 130(29), pp. 9583-9589, (Jul. 23, 2008).

Oleinikov et al, "Self-Assembling Protein Arrays Using Electronic Semiconductor Microchips and in Vitro Translation", J Proteome Res, vol. 2, pp. 313-319, (Apr. 5, 2003).

Sakai, "Theory of gas-diffusion controlled sensitivity for thin film semiconductor gas sensor", Sensors and Actuators B:Chemical, vol. 80, pp. 125-131, (2001).

Samain et al, "Polyfluorophores on a DNA Backbone: Sensors of Small Molecules in the Vapor Phase", Angew Chem Int Ed Engl, vol. 49(39), pp. 7025-7029, (Sep. 17, 2010).

Stern et al, "Label-free biomarker detection from whole blood", Nature Nanotechnology, Advance Online Publication, pp. 1-5, (Dec. 13, 2009).

Timmer et al, "Ammonia sensors and their applications—a review", Sensors and Actuators B, vol. 107, pp. 666-677, (Mar. 16, 2005).

Tomchenko et al, "Detection of chemical warfare agents using nanostructured metal oxide sensors", Sensors and Actuators B, vol. 108, pp. 41-55, (2005).

Wang et al, "Metal Oxide Gas Sensors: Sensitivity and Influencing Factors", Sensors, vol. 10, pp. 2088-2106, (Mar. 15, 2010).

White et al, "Solid-State, Dye-Labeled DNA Detects Volatile Compounds in the Vapor Phase", PLoS Biology, vol. 6 (1), pp. 0030-0036, (Jan. 2008).

Zhang et al, "An integrated chip for rapid, sensitive, and multiplexed detection of cardiac biomarkers from fingerprick blood", Biosensors and Bioelectronics, vol. 28, pp. 459-463, (Jul. 18, 2011).

Mascini et al, "Piezoelectric sensors for dioxins: a biomimetic approach", Biosensors and Bioelectronics, vol. 20, pp. 1203-1210, (Aug. 20, 2004).

Wu et al, "Exploring the recognized bio-mimicry materials for gas sensing", Biosensors & Bioelectronics, vol. 16, pp. 945-953, (2001).

Wu et al, "Synthetic peptide mimicking of binding sites on olfactory receptor protein for use in 'electronic nose'", J Biotechnol, vol. 80, pp. 63-73, (2000).

Office Action issued in U.S. Appl. No. 15/372,343, dated Feb. 1, 2018.

Response to Office Action filed in U.S. Appl. No. 15/372,343, filed May 27, 2018.

Office Action issued in U.S. Appl. No. 15/372,343, dated Aug. 27, 2018.

Office Action issued in U.S. Appl. No. 15/372,343, dated Apr. 8, 2019.

Office Action issued in U.S. Appl. No. 15/372,075, dated Apr. 16, 2019.

Wan, Jin et al. "Silicon nanowire sensor for gas detection fabricated by nanoimprint on SU8/SiO2/PMMA trilayer." Microelectronic Engineering 86 (2009):1238-1242.

* cited by examiner

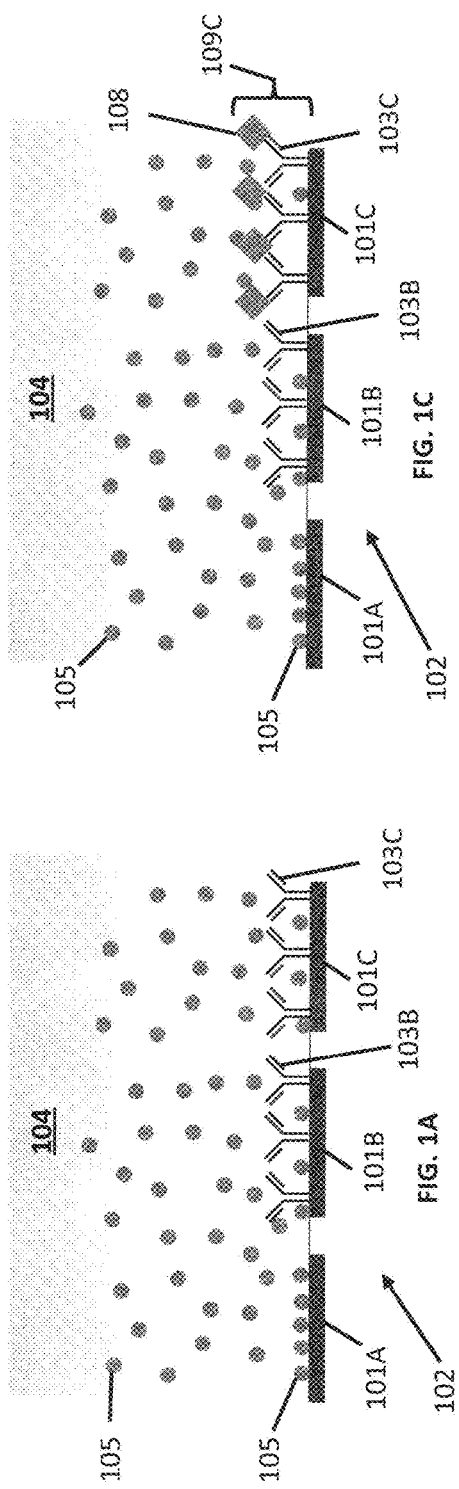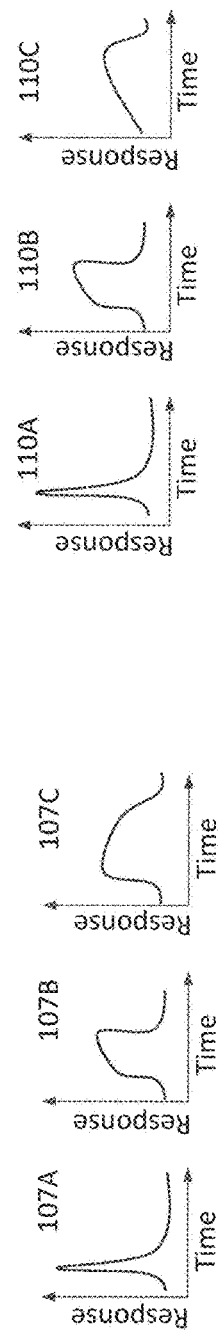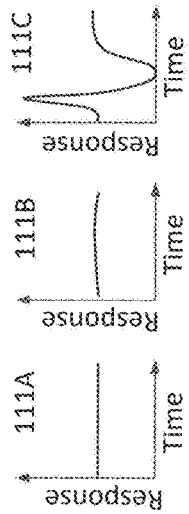

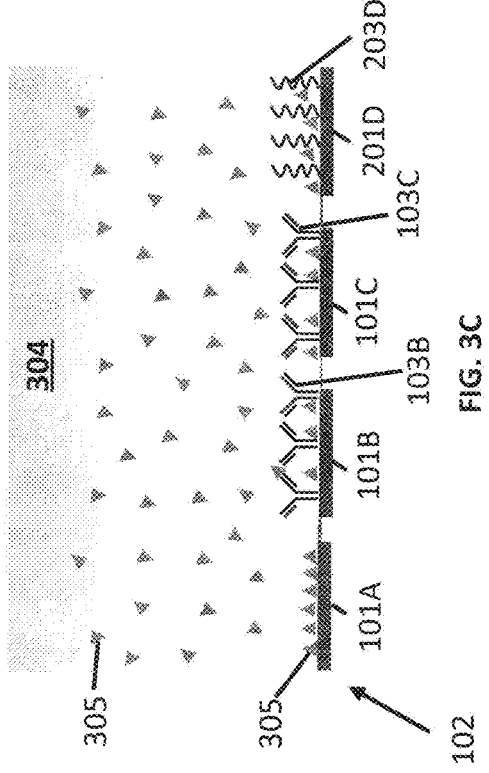
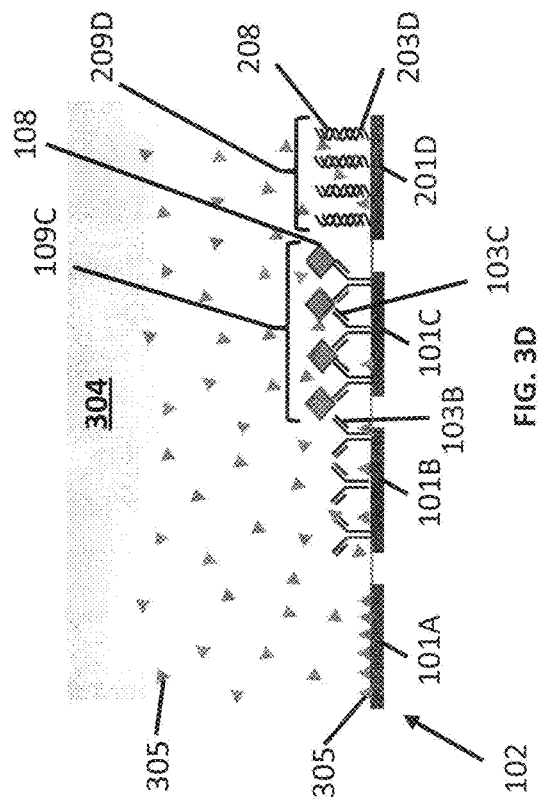
FIG. 3A
FIG. 3B
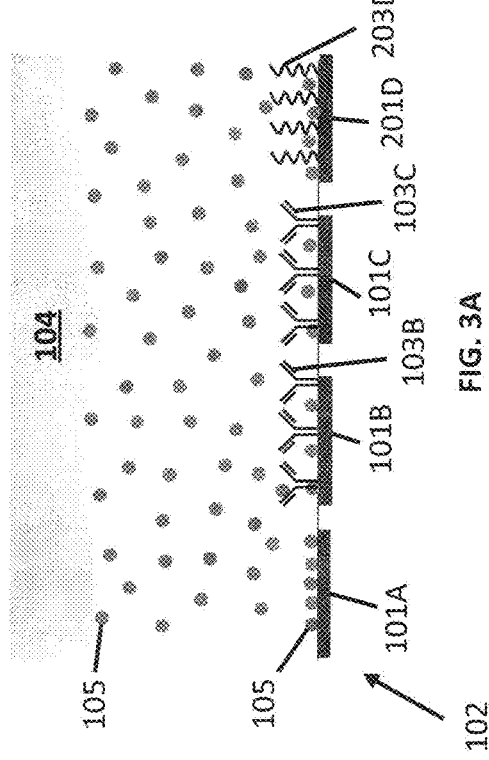
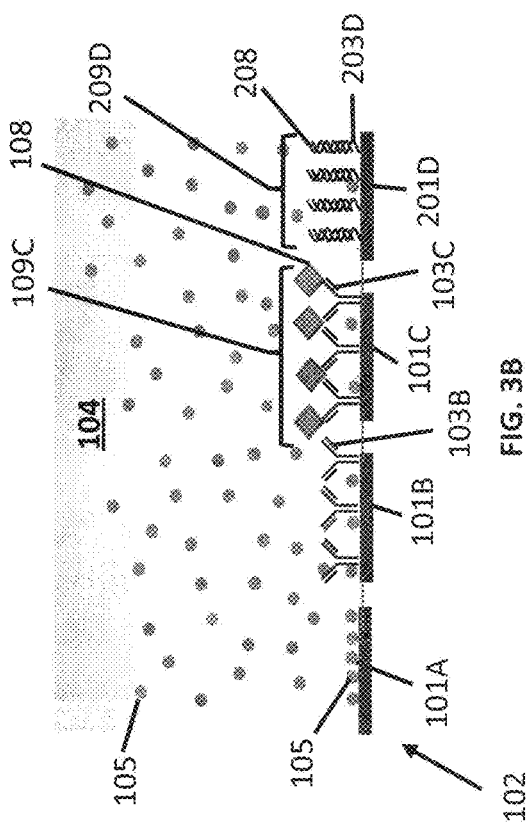
FIG. 3C
FIG. 3D

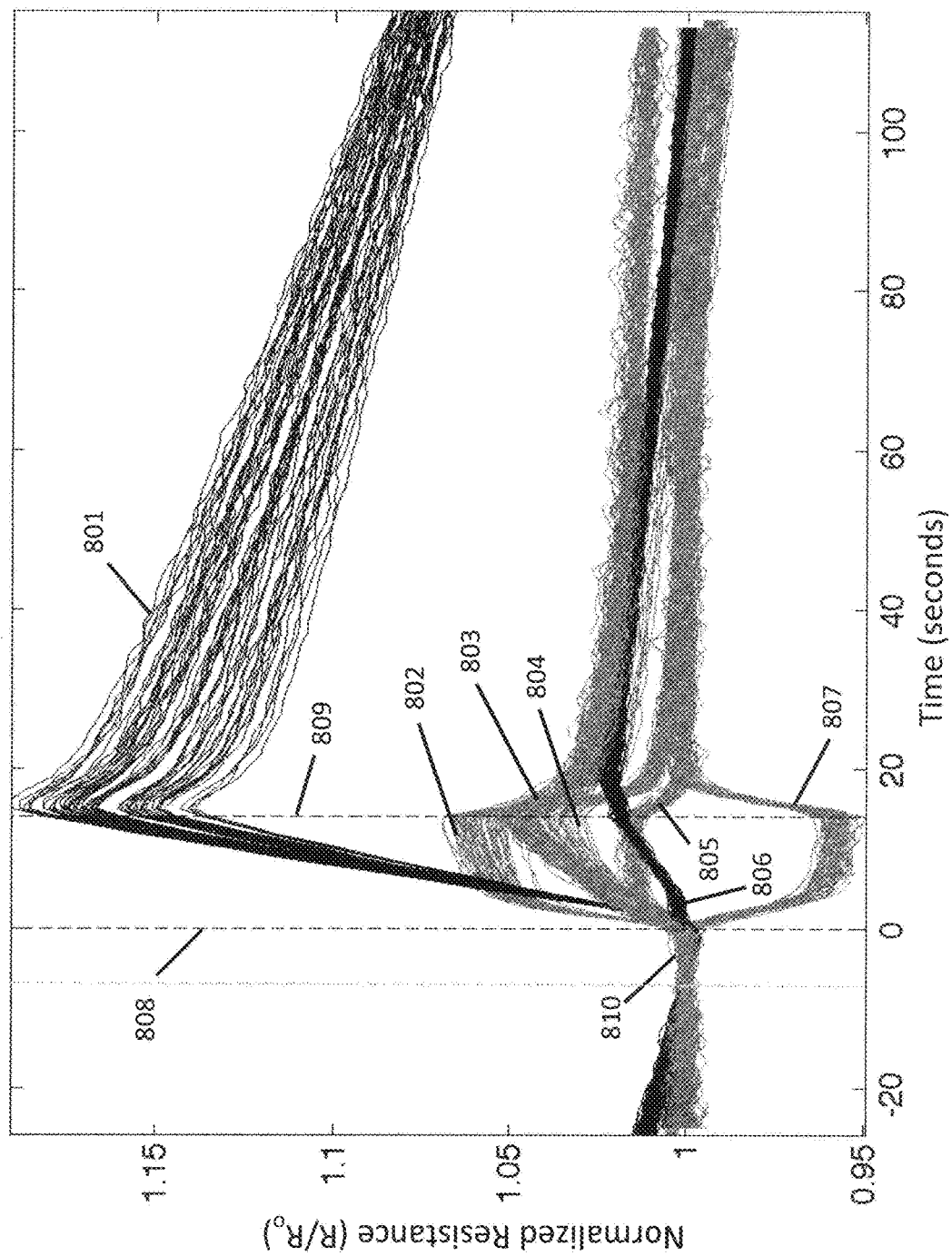

METHODS FOR DETECTING AND QUANTIFYING ANALYTES USING GAS SPECIES DIFFUSION

This application claims priority under 35 U.S.C. § 119 to U.S. Provisional Application No. 62/263,769 filed Dec. 7, 2015, which is incorporated by reference herein in its entirety.

STATEMENT REGARDING FEDERALLY SPONSORED RESEARCH

The invention was made, in part, with government support under Contract No. W81XWH-14-C-0155 DHP awarded by the U.S Army. The government has certain rights in the invention.

FIELD OF THE INVENTION

The invention is related to analyte detection and quantification. Some applications of the invention include the use of methods and sensors of the invention for detecting the presence of, and quantifying chemicals, biomolecules, and other analytes from biological samples and from other types of samples.

GENERAL DESCRIPTION

Methods for detection and quantification of biomarkers include the use of fluorescence labeling, the polymerase chain reaction (PCR), and microarrays of nucleic acids. Many biomarker detection systems employ methods for the direct detection of biomolecules after binding of the biomolecule to a complementary binding partner or receptor. Direct detection of biomolecule binding in these systems may employ detection of radioactive-labeled molecules, electrochemical detection, or optical sensors for measuring changes in fluorescence, chemiluminescence, or color. Many of the current detection systems lack sensitivity and specificity of detection, require bulky instrumentation or instrumentation that is difficult to calibrate, are incompatible with many sample types, and/or are complex, multistep procedures requiring numerous reagents and complicated methods.

Embodiments of the invention include methods, compositions, sensors, and reagents for determining the presence or absence of, and quantifying the amount of an analyte in different types of test samples. By way of example only, biomarker and bioanalyte detection and quantification in biological samples are useful for diagnosing disease, monitoring disease progression, detecting pathogens, and genetic profiling. In embodiments of the invention, binding of an analyte in a test sample to a complementary binding partner (referred to herein interchangeably as "binder" and "analyte binder",) that is present on the surface of a gas sensor results in the formation of a binder-analyte complex. In some embodiments of the invention, methods include exposing a gas sensor that is derivatized with binders, to a control sample of an interrogator gas lacking a complementary analyte, and determining a control gas sensor response profile; exposing a gas sensor derivatized with the binders to a test sample that may comprise an analyte that is complementary to the binders; subsequently exposing the gas sensor to a second sample of the interrogator gas and determining a test sample gas sensor response profile; comparing the control and test sensor response profiles; and determining the presence or absence of and/or quantity of the analyte in the test sample. A difference between the test sample and control response profiles is indicative of the presence of analyte in the test sample. Different species of gases may be used in this manner to enhance detection and quantification of analytes. Methods and sensors of the invention thus enable the indirect detection and reproducible and sensitive quantification of one or more analytes in a test sample.

In embodiments of the invention, a response profile of a gas sensor, or an array of sensors, is determined for selected time periods, ranging from a selected time before exposure of a sensor to an interrogator gas sample to a selected time after stopping exposure of a sensor to an interrogator gas sample. In some aspects of the invention, control and test sample sensor response profiles may be determined multiple times with a single type of interrogator gas or with multiple different interrogator gases.

In some embodiments of the invention, multiple gas sensors derivatized with selected different types of binders for binding selected different analytes are used for determining the presence of and/or quantifying a plurality of analytes in a test sample. In additional aspects of the invention, binders may be present in a porous matrix on a gas sensor. Binders may be deposited or synthesized in situ on a gas sensor or on a porous matrix. In additional aspects of the invention, sensors without binders are used.

In some embodiments of the invention, gas sensors are conductometric semiconducting metal oxide sensors. Metal oxide semiconductor type sensors, also known as Taguchi type sensors (U.S. Pat. No. 3,695,848), are capable of rapidly responding to the adsorption of gas molecules on a sensor surface. Fine et al., (2010 Sensors 10:5469-5502), Liu et al., (2012 Sensors 12(7):9635-9665), and Huang et al., (2009 Sensors 9:9903-9924) describe fabrication and operation of Taguchi type sensors and are incorporated by reference herein in their entirety. Absorption or desorption of a gas on the surface of a metal oxide (e.g., $SnO_2$, $ZnO$, $TiO_2$, $In_2O_3$, and $CuO$) changes the conductivity of the metal oxide material allowing for detection and quantification of gas molecules. Metal oxide semiconductor nanosensors and monolithic arrays of semiconducting nanosensors fabricated on the same substrate, such as the imprinted nanotrace nanosensors and arrays described in Savoy et al., (U.S. Patent App. Pub. No. 2012/0178199A1 and U.S. Pat. No. 8,450,131, both of which are incorporated by reference herein in their entirety), are useful in embodiments of the invention. In some aspects of the invention multiple gas sensors are present in an array of sensors.

In embodiments of the invention, comparison of one or more control gas sensor response profiles with one or more test sample sensor response profiles is used to detect, identify, and/or quantify one or more selected analytes present in a test sample. In additional embodiments of the invention, an analyte in the test sample is quantified. Comparisons of control sample and test sample gas sensor response profiles determined under a variety of conditions enable, contribute to, and enhance detection, identification, and quantification of an analyte in a test sample. In some aspects of the invention, one or more control sensor response profiles and test sample sensor response profiles are stored in a database, and comparing sensor response profiles comprises comparing one or more test sample response profiles to one or more control gas response profiles stored in the database. In additional aspects of the invention, deconvolution of gas sensor response data enables the identification and quantification of gases in a test sample.

In embodiments of the invention, a binder and analyte are complementary and interact in a specific manner. In some aspects of the invention, binders and analytes may be biomolecules, although this is not a requirement of the invention. Test samples for analysis may comprise a biological sample or an environmental sample. Binders useful in embodiments of the invention may be any of numerous types of molecules, compounds, or structures that may be coupled to a gas sensor and that are complementary to an analyte, meaning that the binder is capable of binding to, or otherwise sequestering an analyte in a specific manner.

Other embodiments of the invention are discussed throughout this application. Embodiments described herein are understood to be applicable to all aspects of the invention. It is contemplated that any embodiment discussed herein can be implemented with respect to any method or composition of the invention, and vice versa. Furthermore, compositions of the invention can be used to achieve methods of the invention.

The specification is most thoroughly understood in light of the teachings and references cited within the specification. It should be understood that the drawings, detailed description, and specific examples, while indicating specific embodiments of the invention, are given by way of illustration only, since various changes and modifications within the spirit and scope of the invention will become apparent from this detailed description to those skilled in the art.

Any section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose. To the extent publications and patents or patent applications incorporated by reference contradict the invention contained in the specification, the specification will supersede any contradictory material.

BRIEF DESCRIPTION OF THE FIGURES

The following drawings form part of the present specification and are included to further demonstrate certain aspects of the invention. The invention may be better understood by reference to one or more of these drawings in combination with the detailed description of the specification embodiments presented herein.

FIG. 1A-FIG. 1E is a schematic depiction of an exemplary embodiment of the invention for detection of an analyte using gas sensors present on an array of sensors.

FIG. 3A-FIG. 3D is a schematic depiction of an embodiment of the invention showing the interaction of two different types or species of interrogator gas molecules with an array of sensors.

FIG. 8 shows multiple gas sensor response profiles determined for each of six different volatile organic compound gases and for water, using a sensor derivatized only with linker structures (no binder derivatization).

FIG. 9A shows multiple gas sensor response profiles, determined using a sensor derivatized with linker structures, for each of seven different exemplary interrogator volatile organic gases from common industrial solvents. FIG. 9B shows the averaged gas sensor response profile from all sensors for each interrogator gas. FIG. 9C and FIG. 9D show principal component analysis plots using data from the gas sensor response profiles.

FIG. 10A and FIG. 10B illustrate concentration profile curves representing the concentration distribution of a gas between a gas source and a sensor derivatized with a binder, during gas exposure and diffusion of an exemplary interrogator gas to the sensor (FIG. 10A) and after stopping gas exposure and during diffusion of interrogator gas from the sensor (FIG. 10B). FIG. 10C shows the corresponding gas sensor response profile and the position in time corresponding to each concentration profile curve. In FIG. 10A and FIG. 10B, for ease of viewing, binders are shown as shaded rectangles and the gas is represented as horizontal arrows. Concentration (arb.) (y-axis) refers to concentration represented as arbitrary units. Distances from gas source (x-axis) are in arbitrary units.

FIG. 11A and FIG. 11B are simulations for a sensor having a binder. FIG. 11C and FIG. 11D are simulations for a sensor having a binder-analyte complex. For ease of viewing, the binder and binder analyte complexes are shown as shaded rectangles and the gas is represented as horizontal arrows. Concentration (arb.) refers to concentration represented as arbitrary units. Distances from gas source (x-axis) are in arbitrary units.

DESCRIPTION OF CERTAIN EXEMPLARY EMBODIMENTS

Figure 2A:
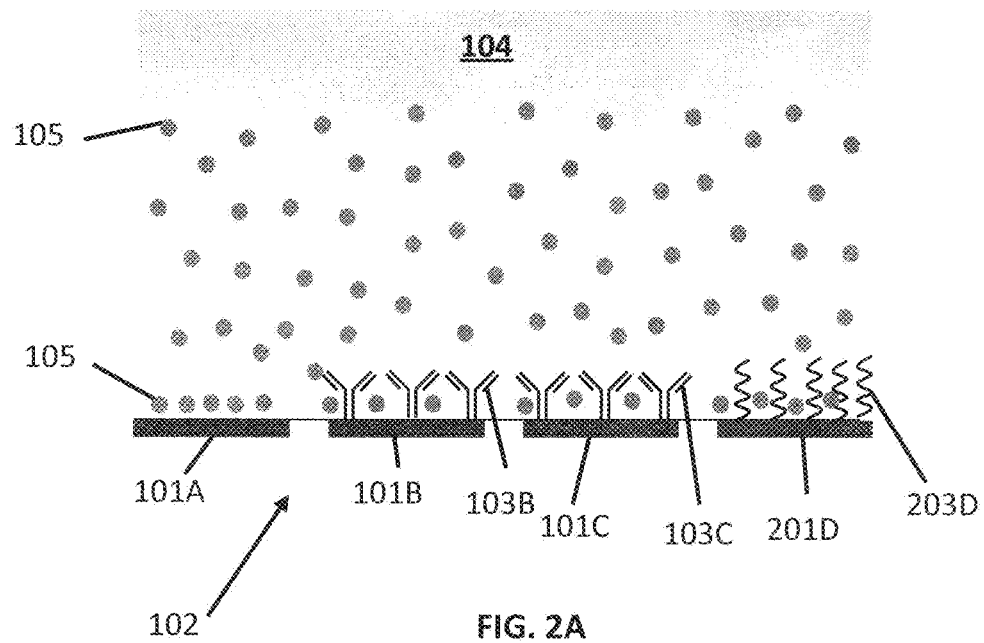
FIG. 2A-FIG. 2B is a schematic depiction of one embodiment of the invention in which a gas sensor array comprises sensors having different types of biomolecule binders and shows the binder-analyte complexes that are formed upon exposure to a test sample having selected complementary analytes.

Reference will now be made in detail to certain exemplary embodiments of the invention, some of which are illustrated in the accompanying drawings. To assist in understanding the present invention, certain terms are first defined. Additional definitions are provided throughout the application.

The use of the word "a" or "an" when used in conjunction with the term "comprising" in the claims and/or the specification may mean "one," but it is also consistent with the meaning of "one or more," "at least one," and "one or more than one." The use of the term "at least one" in the specification and claims is meant to include "one or more than one", and the use of the term "one or more than one" is meant to include "at least one".

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or." It is also contemplated that anything listed using the term "or" may also be specifically excluded.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

As used herein, the terms "sensor", "gas sensor", "nanosensor", "gas detector", "detector" and combinations of these are used interchangeably and refer to a gas sensor, or a gas sensor surface that interacts with a gas molecule.

The term "analyte" encompasses biomarkers, small molecule metabolites, antigens, proteins, peptides, polypeptides, antibodies, nucleic acids, chemical compounds such as hormones, cytokines, lipids, pharmaceutical compounds (e.g., drugs), sugars, acids, bases, and other molecules that can bind to binders. The presence of one or more analyte in a test sample may be determined, and the amounts of analytes may be quantified using methods and compositions of the invention.

As used herein, the terms "binder" and "analyte binder" refer to biomarkers, biomolecules, small molecule metabolites, cytokines, hormones, lipids, proteins, peptides, polypeptides, antibodies, nucleic acids, chemical compounds, pharmaceutical compounds (e.g., drugs), sugars, acids, bases, and other entities that may be present on, or bound, to a detector surface and that are "complementary" to an analyte, meaning that the binder is capable of binding to, or otherwise sequestering, an analyte in a selective or specific manner. The terms "binder-analyte" and "binder-analyte complex" refer to a complex comprising an analyte and binder held together, or bound to, one another. By way of example only, a single-stranded nucleic acid binder will bind in a specific manner with a nucleic acid analyte that is complementary to the nucleic acid binder, forming an analyte-binder complex. Similarly, an antibody binder may recognize and interact in a specific manner with an epitope on a protein analyte and, form an analyte-binder complex. Other specific, complementary interactions between molecules, including biological molecules, are known to those of skill in the art.

In some embodiments of the invention, a gas sensor is derivatized with binders that are anchored to or attached to the gas sensor. Subsequently, exposure of the binder-derivatized gas sensor to a test sample comprising an analyte results in binding or sequestration of the analyte by the binder. A sample of a known interrogator gas is then introduced to a sample chamber having the sensor, and interrogator gas molecules diffuse through the binder-analyte complex to the sensor surface and contact the surface, thereby creating an electrical response based on a change in electrical resistance or conductance of the gas sensor due to adsorption of the gas molecules on the sensor surface.

In some embodiments of the invention, bound analyte is indirectly detected by a method comprising the steps of (1) exposing a gas sensor derivatized with binders, to a control sample comprising a known interrogator gas and lacking a complementary analyte, and determining a control gas sensor response profile, (2) exposing the binder-derivatized gas sensor to a test sample that may comprise analytes complementary to the binders, (3) after exposing the sensor to the test sample, subsequently exposing the gas sensor to a second sample comprising the interrogator gas and determining a second gas sensor response profile, referred to as a "test sample gas sensor response profile", (4) comparing the control gas sensor response profile and the test gas sensor response profiles, and (5) determining the presence or absence of and/or quantity of the analyte in the test sample. A difference between the test sample and control sensor response profiles is indicative of the presence of analyte in the test sample. In additional embodiments of the invention, comparison of a test sample response profile and a control response profile enables quantification of the analyte in the test sample. Different gas molecules may be used in this manner to enhance detection and quantification of analytes.

As used herein, "test sample" refers to a sample that is analyzed to determine the presence of, identity of, and/or quantity of one or more analytes in the sample, and "control sample" refers to a sample that comprises at least one known gas species, also referred to as an "interrogator" gas, and that lacks an analyte that is complementary to a binder on the gas sensor.

In embodiments of the invention, a gas sensor response profile is determined for a selected time period, ranging from a selected time before exposure of a sensor to a gas sample to a selected time after stopping gas flow. Gas sensor response profiles are determined by measuring a sensor parameter, such as for example resistance, current, capacitance, or electrochemical potential from the selected time before exposure of a sensor to a gas to the selected time after stopping gas flow. In embodiments of the invention, response of a gas sensor to a gas molecule requires interaction of the gas molecule with the sensor. In certain aspects of the invention, multiple gas sensor response profiles may be determined and/or recorded in succession, such as for example to record sensor responses to multiple gas exposures. In embodiments of the invention, sensor response profile data may be represented as a plot of sensor response data, e.g., current or resistance vs. time. As used herein, "gas sensor response profile" means the gas sensor response data and associated data determined as described above. "Gas sensor response profile" may also mean a graphical representation or other representation of the determined gas sensor response data and associated data.

In embodiments of the invention, a gas sensor response profile that is determined during exposure of a gas sensor to a control sample comprising a known interrogator gas is referred to interchangeably as a "control sample response profile", a "control sensor response profile", or a "control sample sensor response profile". A "test sample gas sensor response profile", also referred to herein, interchangeably, as a "test sample response profile" or a "test sample sensor response profile" is a sensor response profile that is determined during a second exposure of the sensor to a sample of the known interrogator gas, wherein the second exposure of interrogator gas occurs after exposing the gas sensor to a test sample and allowing for binding of any analyte, which may be present in the test sample, to a binder on the sensor.

As used herein, "exposing" or "exposure of" a gas sensor to a gas sample comprises bringing the gas sample in proximity to the gas sensor to allow for gas molecules to adsorb to the sensor, such as for example by introducing a gas sample to a chamber in a manner that allows for diffusion of gas molecules to a sensor surface and adsorption of gas molecules on the sensor surface. The term "exposing" encompasses "contacting". Exposing a sensor to a gas sample encompasses contacting the sample with the sensor and contacting the sensor with the sample.

FIG. 1A-FIG. 1E is a schematic depiction of an exemplary embodiment of the invention for detection of an analyte using gas sensors present on an array of sensors. In this exemplary embodiment (FIG. 1A), gas sensors 101B, 101C are present on gas sensor array 102 and are derivatized with binders 103B, 103C. In some aspects of the invention, no binder is present on a sensor, as illustrated by the underivatized, bare gas sensor 101A. One or more gas sensors on an array may not comprise a binder. Upon exposing the sensors to a control sample comprising a known interrogator gas 105, interrogator gas molecules 105 diffuse directly from gas source stream 104 (in the case of sensor 101A lacking a binder), or through binders 103B and 103C, to sensors 101A, 101B, 101C, whereupon surface-adsorbed gas molecules elicit a response by sensors 101, due to a change in electrical conductance of the gas sensors (i.e., a "gas sensor response").

FIG. 1B shows exemplary control sample sensor response profiles 107A, 107B, 107C from sensors 101A, 101B, 101C that would be determined with exposure of underivatized gas sensor 101A and binder-derivatized gas sensors 101B and 101C to a control sample comprising the interrogator gas (i.e., a control gas sample, comprising a known concentration of a known interrogator gas 105, that does not comprise an analyte). In some embodiments of the invention, response profiles may be determined and recorded as measurements of electric current as a function of time. After stopping gas flow from gas source stream 104, and optionally purging gas molecules 105 from sensors 101, gas sensor response returns to baseline. Purging may occur by simple diffusion or by introduction of a purge gas such as clean, dry air, or by evacuating gas from the sensor surface. Purging may be unassisted or may be accelerated by a heater in contact with sensor array 102.

As depicted in FIG. 1C, sensor array 102 is then exposed to a test sample which may comprise analyte 108 that binds selectively to complementary binder 103C on gas sensor 101C forming binder-analyte complex 109C. In this example, analytes that would bind to binder 103B on gas sensor 101B are not present in the test sample. After exposure of sensors 101 to the test sample, sensor array 102 is exposed a second time to a sample of interrogator gas molecules 105 from gas source stream 104, and gas molecules 105 will again diffuse to the surface of sensors 101A, 101B, and 101C. Test sample gas response profiles 110A, 110B, and 110C are determined after exposure to the test sample and after the formation of binder-analyte complex 109C (comprising analyte 108 and binder 103C) (FIG. 1D). Ratiometric comparisons of control sample sensor response profiles 107A, 107B, 107C and the corresponding test sample sensor response profiles 110A, 110B, 110C yield gas sensor response profile differentials 111A, 111B, 111C (FIG. 1E) that can be analyzed to determine the presence or absence of an analyte 108 in a test sample. A ratiometric comparison represents the ratio of a control sensor response profile to a test sample sensor response profile or the ratio of a test sample sensor response profile to a control sensor response profile. In some embodiments of the invention in which multiple sensors are used, averaged, normalized sensor response profiles are used for ratiometric comparisons. FIG. 1E schematically depicts that the ratiometric comparison 111C between sensor response profiles 107C and 110C illustrates significant differences between those sensor response profiles. In additional aspects of the invention, further quantitative analysis may be performed to determine the amount of bound analyte 108 in binder-analyte complex 109C using differential comparative data analytical methods such as principal component analysis and other numerous methods well-known in the art.

In some embodiments of the invention, gas detectors or gas sensors comprise structures having nanoscale dimensions. Exemplary nanoscale structures include nanotubes, nanowires, nanorods, nanofibers, and nanotraces and are referred to herein generally as "nanostructures". Gas detectors that have nanostructures as gas sensors are also referred to herein as "nanosensors" or "gas nanosensors". Nanostructures have at least one cross sectional dimension, at some point along their length that is less than about 1,000 nm (1 micron). In some embodiments of the invention gas sensors comprise nanostructures having cross-sectional dimensions less than about 500 nm, less than about 250 nm, less than about 100 nm, less than about 50 nm, less than about 10 nm, or less than about 5 nm. In some aspects of the invention, the cross-sectional dimension is from about 0.5 nm to about 1 nm or from about 1 nm to about 5 nm. In some embodiments of the invention, nanostructure lengths range from 1 nm to 100 microns, including any selected size range therebetween. It is specifically contemplated that cross sectional dimensions of nanostructures may be any size in the ranges listed above, including the higher and lower limits listed. All size ranges described are inclusive of the lower and upper limit values. Size ranges within the larger ranges listed above are also contemplated to be useful in some embodiments of the invention. Specific size ranges may be useful in specific aspects of the invention.

In embodiments of the invention, materials useful for gas sensors should be amenable to the attachment of a binder to the sensor surface in a manner that preserves functionality of the binder for binding a complementary analyte. Desirable materials for use in gas sensors include those that exhibit changes in parameters such as resistance, current, capacitance, or electrochemical potential upon interaction with a gas. Exemplary materials include various forms of semiconducting carbon, conducting polymers, Group IV semiconducting materials, semiconducting oxides, semiconducting nitrides and other transition metal II-VI and III-V semiconductor compounds. In some aspects of the invention, gas sensors comprising one or more of conducting polymers, non-conducting polymers, carbon composites, carbon nanotubes, and gold, or other noble metal catalytic particles may be useful in embodiments of the invention (Savoy et al., U.S. Pat. No. 8,450,131; Hatchett and Josowicz, Chem Rev (2008) 108:746-769; Yoon, Nanomaterials (2013) 3:524-549.).

In some embodiments of the invention, a gas sensor may be a conductometric semiconducting metal oxide ($MO_x$) sensor. Mechanisms of gas detection by semiconducting $MO_x$ gas sensors useful in embodiments of the invention are known in the art and have been recently reviewed (Wang et al., Sensors (2010) 10:2088-2106; Liu et al., Sensors (2012) 12:9635-9665; Huang and Wan, Sensors (2009) 9:9903-9924; Fine et al., (2010) 10:5469-5502). Gas detection by these types of sensors is based on the detection of a change in electrical resistance or conductance caused by interaction of gas molecules with the gas sensor surface. Methods and materials for making conductometric semiconducting $MO_x$ nanotrace sensors using nanoimprint lithography, including materials useful as sensor surfaces and substrates and nanosensor dimensions, are described in Savoy et al., U.S. Pat. No. 8,450,131, which is incorporated by reference herein in its entirety. $MO_x$ nanotrace sensors have greater surface area-to-volume ratios compared to thin films of thin film sensors, permitting rapid interfacial gas exchange compared to diffusion between bulk grain boundaries and enabling the rapid collection of gas sensor response profiles. Furthermore, high surface area-to-volume dimensions can eliminate the need for repeated heat cycling of a gas sensor, which can degrade calibration over time as the grain structure changes. Temperature cycling above ~100° C. can also degrade biomolecules. In other embodiments of the invention, gas sensors may comprise materials other than, or in addition to, semiconducting metal oxides. Although $MO_x$ nanotrace sensors patterned by nanoimprint lithography have advantages in some aspects of the invention, in other aspects of the invention, nanostructure grain dimensions of thin film materials may also be useful as a gas detector. In some embodiments of the invention, methods of the invention may be implemented with sensors that are not nanoscale-dimensioned.

In some embodiments of the invention, gas sensors may be assembled into an array on a substrate. The number of sensors in an array can range from one to hundreds, to thousands, to millions depending on the application and device parameters, such as the number of the read-out circuits. The number of nanosensors in an array may include any number in the range from one to millions, including one and millions. Further embodiments may involve deposition of sensors on the surface of CMOS read-out integrated circuits which may comprise by way of example only, arrays of 3×3, 10×20, 40×60, 320×540, 640×480 VGA, 2056×1560 full size, 2592×3872 10 megapixel, and 3456×5184 18 megapixel. Gas sensors may be configured with aspect ratios of 1×2, 1×3, 1×4, 1×8, 1×32, 1×100, 1×500, 1×1000, 1×10,000, 2×3, 3×4, and 9×16. Sensors may be grouped together in any of a variety of numbers and array sizes and shapes. In some embodiments of the invention, selected nanosensors in an array can be employed as references and controls. There is no limit on the number of gas sensor pixels or the aspect ratio of the sensors in an array 102 of sensors.

In embodiments of the invention, a sensor in an array may be derivatized with any selected type of binder selected for specific interaction with an analyte in a test sample, may be derivatized with linker structures 401, or a may be an underivatized, bare sensor. In some aspects of the invention, a single gas sensor or multiple gas sensors are derivatized with a single selected "species" or "type" of binder. In other aspects of the invention, multiple sensors in an array are derivatized with the same selected species of binder. In still other aspects of the invention, multiple sensors in an array on a substrate may be derivatized with different selected types of binders. In additional aspects of the invention, multiple sensors derivatized with the same type of binder may be grouped together on a selected region of an array. In still other aspects of the invention, an array of sensors may comprise multiple groups of sensors, each group derivatized with a different, selected type of binder. In certain aspects of the invention, one or more gas sensors may be underivatized sensors. When referring to gas sensors, the terms "underivatized" and "underivatized sensor" mean that the sensor is a bare sensor with no attached molecules. Exemplary methods for arranging nanosensors and groups of nanosensors on an array are described in Savoy et al., U.S. Pat. No. 8,450,131.

Figure 2B:
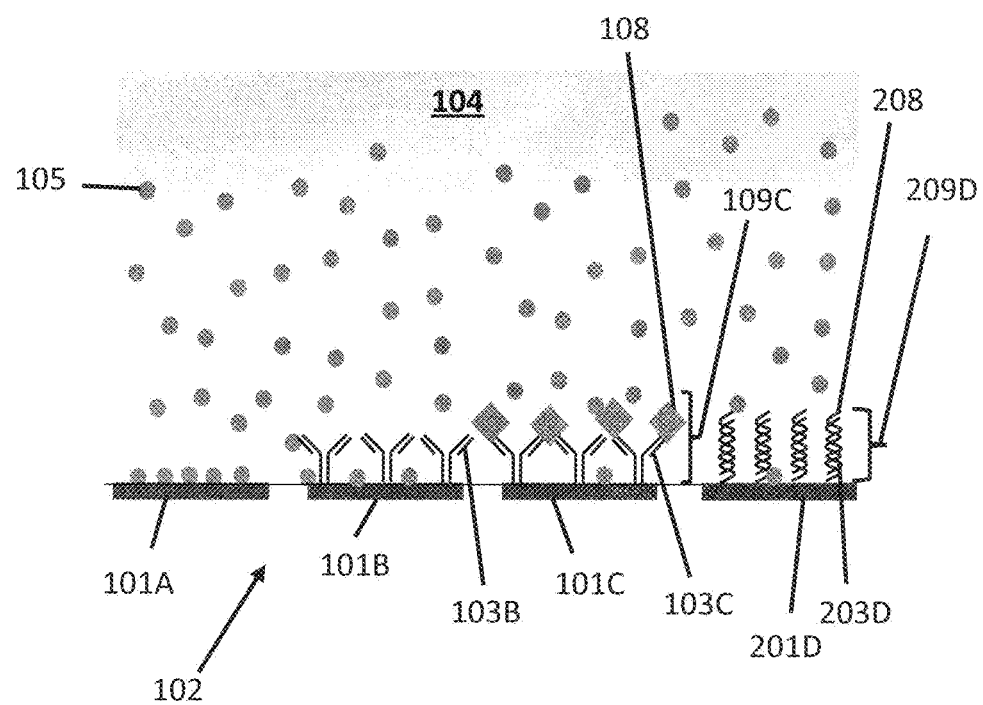

FIG. 2A-FIG. 2B is a schematic depiction of one embodiment of the invention in which a gas sensor array comprises sensors having different types of biomolecule binders and shows the binder-analyte complexes that are formed upon exposure to a test sample having selected complementary analytes. In the exemplary embodiment shown in FIG. 2, in addition to antibody binders 103B, 103C coupled to sensors 101B and 101C respectively (FIG. 2A), a nucleic acid binder 203D is shown coupled to sensor 201D. During exposure of sensor array 102 to a test sample comprising analyte 108, as shown in FIG. 2B, binder-analyte complex 109C forms. If present in the test sample, analyte 208 and binder 203D will also form binder-analyte complex 209D. In this exemplary aspect of the invention, analyte 208 is a nucleic acid that is complementary to nucleic acid binder 203D such that analyte-binder complex 209D is formed (FIG. 2B) during exposure to the test sample.

In embodiments of the invention, exposing a sensor to a test sample comprises bringing the test sample in proximity to the gas sensor to allow for analyte that may be in the test sample to bind to binder present on the sensor surface. The term "exposing" encompasses "contacting". Exposing a sensor to a test sample encompasses contacting the sample with the sensor and contacting the sensor with the sample. In some embodiments of the invention, exposing a sensor to a test sample comprises introducing a test sample, in a liquid, into a sample chamber with the sensor or passing the sample over a sensor or sensor array. Alternatively, exposing a sensor to a test sample may comprise introducing a stream of gaseous sample into a chamber in contact with a sensor surface.

In some aspects of the invention, a test sample suspected of having an analyte of interest, may be allowed to contact a gas sensor (e.g., by incubating the sample with a sensor) for a selected period of time under a selected set of conditions to allow or enhance binding of an analyte to a binder. Liquid samples to be assayed can be of any volume appropriate for the size of the sensor. Sensors are exposed to test samples under physical and chemical conditions effective for achieving binding or other stable interaction of the binder and the complementary analyte. In some aspects of the invention, to enhance formation of specific binder-analyte complexes at different sensors and to prevent or limit non-specific binder-analyte complex formation, it may be necessary to adjust physical or chemical parameters, which may include for example, solution composition (e.g., sample buffer type, pH, salt concentration, and ionic strength), gaseous sample composition, length of and temperature of exposure or incubation, number and composition of washes after test sample exposure and prior to exposure with the interrogator gas. These conditions are routinely determinable.

In some aspects of the invention, multiple different types of binder-analyte complexes may be capable of forming during a single test sample exposure under the same exposure conditions. In other aspects of the invention, it may be advantageous or necessary to expose an array of sensors having different types of binders to a test sample under a variety of different exposure conditions, for example by sequentially exposing the array of sensors to a test sample. After incubation, the sensors can optionally be treated (e.g.; washed) to remove unbound sample components, using conditions that are determined empirically to leave specific interactions intact, but to remove non-specifically bound material. For example, samples can be washed between about one and ten times or more under the same or somewhat more stringent conditions than those used to form the analyte-binder complex.

FIG. 3A-FIG. 3D is a schematic depiction of an embodiment of the invention showing the interaction of two different types or species of interrogator gas molecules with an array of sensors. In some embodiments of the invention, as illustrated in FIG. 3A and FIG. 3B, gas sensors 101A, 101B, 101C, 201D that are assembled as an array 102 may be exposed to a single type of gas molecules 105 from gas source stream 104. In other aspects of the invention, as shown in FIG. 3C and FIG. 3D, sensors 101, 201 may be additionally exposed to a different type of interrogator gas molecules 305 from a different gas source stream 304. Interaction of interrogator gas molecules 105, in a control gas sample having no analyte, with sensors 101, 201 (as depicted in FIG. 3A) will result in control sensor response profiles that are different from the control sensor response profiles produced when interrogator gas molecule 305, in a control gas sample having no analytes, interacts with sensors 101, 201 (FIG. 3C). Similarly, after exposure of sensor array 102 to a test sample containing analytes 108 and 208 and formation of binder-analyte complexes 109C and 209D, subsequent exposure of sensors 101, 201 to interrogator gas molecule 105 (FIG. 3B) will result in test sample response profiles that are different from the test sample response profiles produced when the sensors are subsequently exposed to interrogator gas molecule 305 (FIG. 3D). Gas sensor response profile differentials (not shown for FIG. 3, but determined by ratiometric comparison as for those shown in FIG. 1E) between control sensor response profiles and test sample sensor response profiles will be different with each different type of interrogator gas molecule used and in some aspects of the invention may provide additional means for determining the presence of and quantification of analytes in a test sample. Differences in test sample sensor response profiles and control sensor response profiles are observed when analytes are present in a test sample and form binder-analyte complexes 109 and 209 on sensors 101C and 201D, respectively.

Figure 4A:
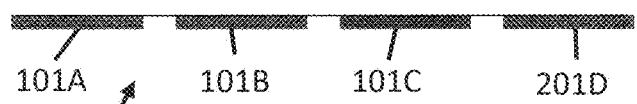
FIG. 4A-FIG. 4C is a schematic depiction of one embodiment of the invention for covalently anchoring binders to gas sensors present as an array of sensors.
Figure 4B:
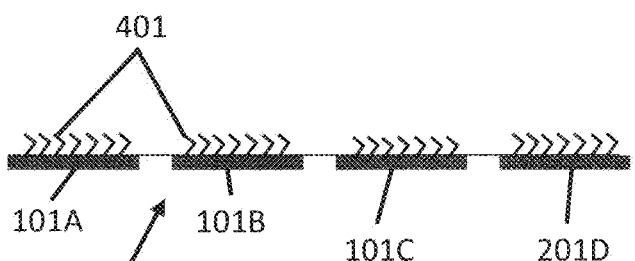
Figure 4C:
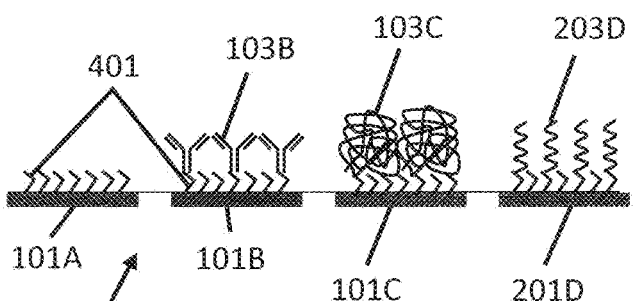

FIG. 4A-FIG. 4C is a schematic depiction of one embodiment of the invention for covalently anchoring binders to gas sensors present as an array of sensors. In this exemplary embodiment, gas sensors 101A, 101B, 101C, 201D, present on gas sensor array 102 (FIG. 4A) are initially derivatized with linker structures 401 on their surfaces as depicted in FIG. 4B. In some aspects of the invention, linker structures 401 may facilitate the attachment of binders, 103B, 103C, 203D to a nanosensor and/or the synthesis of binders directly on the sensor (FIG. 4C). In some aspects of the invention, coupling of binders to linkers is mediated by chemisorption, and in other aspects of the invention coupling is mediated by physisorption. Heterobifunctional linker structures useful for covalent attachment of chemical and biological structures to surfaces are known and are commercially available (e.g., from Sigma-Aldrich Co. LLC, St. Louis, Mo., USA). Exemplary linker structures 401 include silanes, glutaraldehydes, succinimides, carboxylates, epoxies and phosphonates, to name only a few. In other aspects of the invention, no binder is present on a sensor surface, as illustrated by gas sensor 101A in FIG. 4B and FIG. 4C, having only linker structures 401.

In some embodiments of the invention, it is specifically contemplated that a binder is not a biomolecule. In additional embodiments of the invention, binders for use in embodiments of the invention include biomolecules, biomarkers, small molecule metabolites, cytokines, hormones, lipids, proteins, peptides, polypeptides, antibodies, nucleic acids, aptamers, polymers, chemical compounds, organic compounds, pharmaceutical compounds (e.g., drugs), or other entities that are covalently linked to, synthesized on, or otherwise coupled to a detector surface and that are "complementary" to an analyte, meaning that the binder is capable of binding to, or otherwise sequestering an analyte in a specific manner.

In some aspects of the invention, a binder is a cell or a part thereof, such as by way of example only, a cell membrane or a fragment thereof, a liposome, a nucleus, an organelle, a protein, a receptor molecule, or another subcellular component. Binders may be isolated from cells or may be synthetically prepared. Methods for in vitro synthesis of small molecules, antibodies, peptides, nucleic acids, cell membranes, membrane mimics, liposomes, and other biological and chemical structures are known in the art.

In some embodiments of the invention, binder 103, 203 is synthesized in situ on a nanosensor, with or without linkers. In some aspects of the invention, binders may be peptides 103C or nucleic acids 203D that are synthesized in situ on the nanosensor. In certain aspects of the invention, peptides synthesized on a nanosensor surface may comprise, at least 2, 3, 4, 5, 6, 7, 8, 9, 10, 15, 20, 25, 30, 35, 40, 45, 50, 60, 70, 80, 90, or 100 amino acids or any number therebetween and inclusive of the smaller and larger sizes listed. In other aspects of the invention, peptide length is not limited and may be any length that retains functionality as an analyte binder and that can be synthesized on, or attached to, the surface of nanosensor. Similarly, in certain aspects of the invention, nucleic acids synthesized on a nanosensor may comprise, at least 2, 3, 4, 5, 6, 7, 8, 9, 10, 15, 20, 25, 30, 35, 40, 45, 50, 60, 70, 80, 90, or 100 nucleotides or any number therebetween and inclusive of the smaller and larger sizes listed. In other aspects of the invention, nucleic acid length is not limited and may be any length that retains functionality as an analyte binder and that can be synthesized on, or attached to, the surface of a nanosensor. Representative methods for synthesizing peptides and nucleic acids on surfaces can be found in Gao et al., (Proteomics, (2003) 3:2135-2141), and Gao et al., (U.S. Pat. No. 6,426,184), both of which are incorporated by reference herein in their entirety. Other synthesis methods are known to those with skill in the art.

In other embodiments of the invention, binders are spotted onto a gas sensor. Peptide, protein, and nucleic acid binders useful for spotting onto a nanosensor are typically not limited by size, length, shape, or sequence as long as they can be spotted onto the sensor and bind to or sequester an analyte.

In additional embodiments of the invention, other methods may be used to position binders on sensors 101, 201. Binders may be confined in or otherwise coupled to a porous support matrix on the gas sensor surface, or may be confined in or otherwise coupled to a porous matrix then positioned, or registered to a gas sensor surface.

Figure 5A:
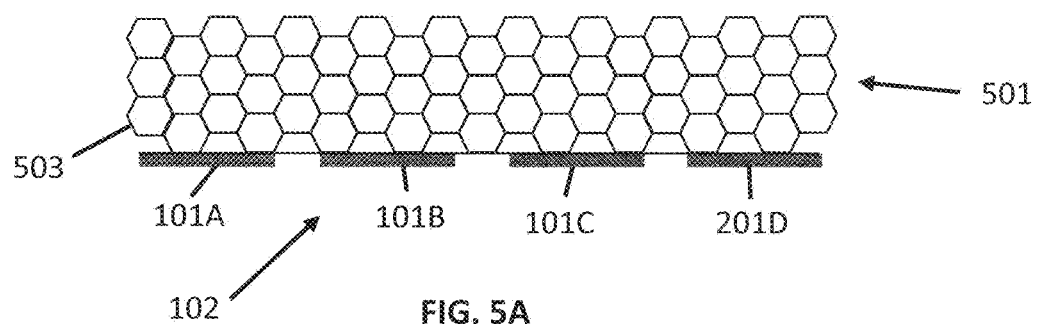
FIG. 5A-FIG. 5C is a schematic depiction of an embodiment of the invention in which a gas sensor array comprises sensors having multiple biomolecule binder types coupled to a porous support matrix present on gas sensors in a sensor array.
Figure 5B:
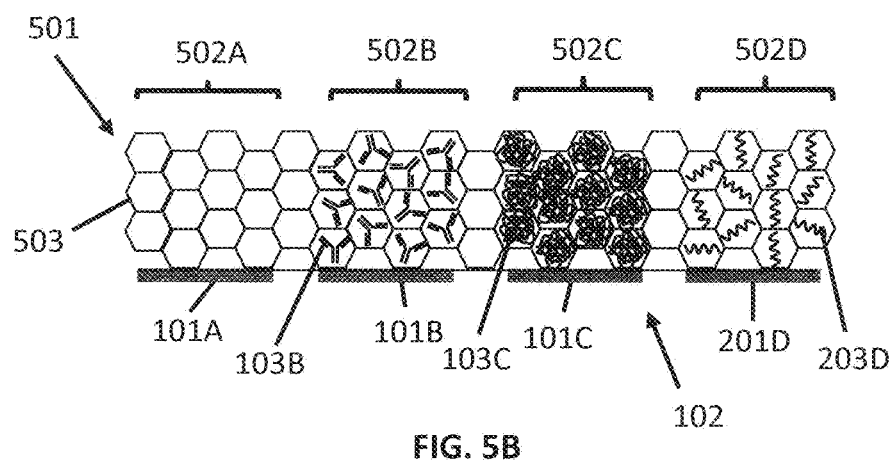
Figure 5C:
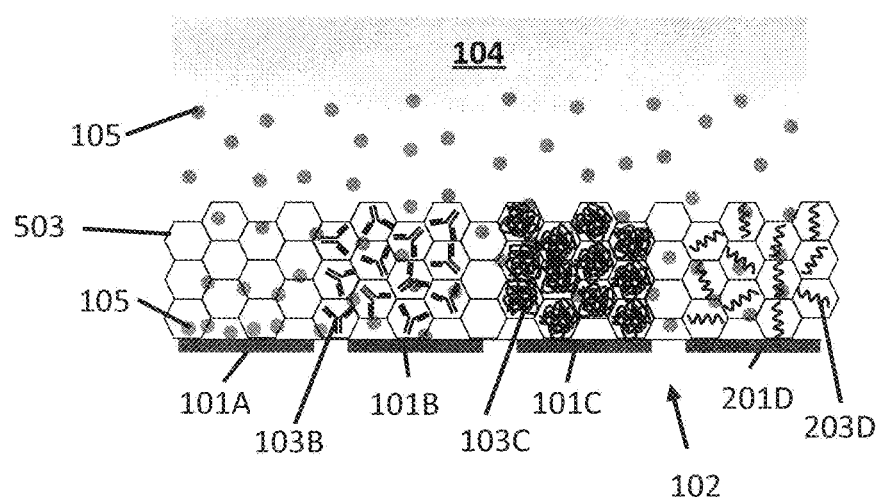

FIG. 5A-FIG. 5C is a schematic depiction of an exemplary embodiment of the invention in which a gas sensor array comprises sensors having multiple biomolecule binder types coupled to a porous support matrix present on gas sensors in a sensor array. FIG. 5A shows an exemplary embodiment of the invention in which a porous support matrix 501, also referred to herein as "porous matrix", is first deposited on sensor array 102. Binders 103, 203 are dispensed onto and/or dispersed into select regions 502B, 502C, 502D of deposited porous support matrix 501 and subsequently coupled to the porous matrix (FIG. 5B). In some embodiments of the invention, binders are dispensed to deposited porous support matrix 501 that is present on selected sensors so that selected types of binders are in registration with selected sensors of sensor array 102. Numerous methods may be used for dispensing, dispersing, and coupling binders to, or for directly synthesizing binders on, deposited porous support matrix 501. Some exemplary methods include spotting, inkjet printing, drop-casting, silkscreen printing, gravure printing, and flexographic printing. In some aspects of the invention, binders are dispensed to deposited porous support matrix 501 using a bioink.

In some embodiments of the invention, covalent coupling of binders to porous support matrix 501 may be employed to couple the binders to structural segments 503 of porous support matrix 501. By way of example only, covalent coupling to structural segments 503 may be mediated by one or more of numerous anchoring chemistries well known in the art, such as silane heterobifunctional crosslinkers, succinimides, glutaraldehyde, and epoxies. Other types of structures for coupling binders to structural segments 503 of deposited porous matrix 501 include silanes, peptides, nucleotides, carbohydrates, and phosphonates to name only a few. Covalent coupling yields binders permanently attached to deposited porous support matrix 501. In some aspects of the invention, coupling of binders to porous support matrix 502 is mediated by chemisorption, such as for example by covalent coupling, and in other aspects of the invention coupling is mediated by physisorption.

In certain aspects of the invention, materials used for porous support matrix 501 have a high surface area for coupling binders. Porous matrix 501 may comprise biomolecules, crosslinked biomolecules, non-biological material, or mixtures thereof that contain an interconnected network of volumetric space. In some aspects of the invention, structural segments 503 of deposited porous matrix 501 comprise glass, polymer, or composite fibers and may form a mat or sheet. Fibers may be woven or may form a random matrix. In additional aspects of the invention, deposited porous support matrix 501, may comprise beads. In some aspects of the invention, the porosity and thickness of porous matrix 501 may be adjusted and may alter the traversal of the matrix by gas molecules 105 from source 104 prior to the adsorption of gas molecules on the surface of sensor 101A, 101B, 101C, and 201D (FIG. 5C) thereby affecting a control sample or test sample gas sensor response profile. In some aspects of the invention, no binders are dispensed to porous matrix 501, such as in region 502A over select sensor surface 101A (FIG. 5B). In this exemplary aspect of the invention, sensor 101A is derivatized only with porous support matrix 501.

Figure 6A:
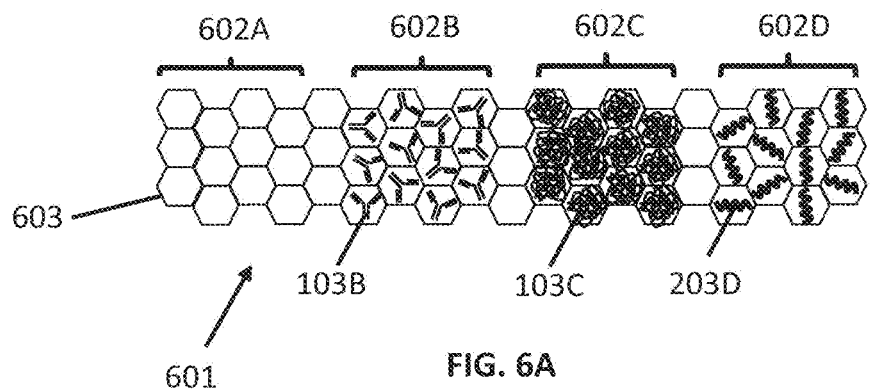
FIG. 6A-FIG. 6C is a schematic depiction of an embodiment of the invention in which multiple biomolecule binder types are coupled to a freestanding porous matrix, which is then registered to specific sensors in the array.
Figure 6B:
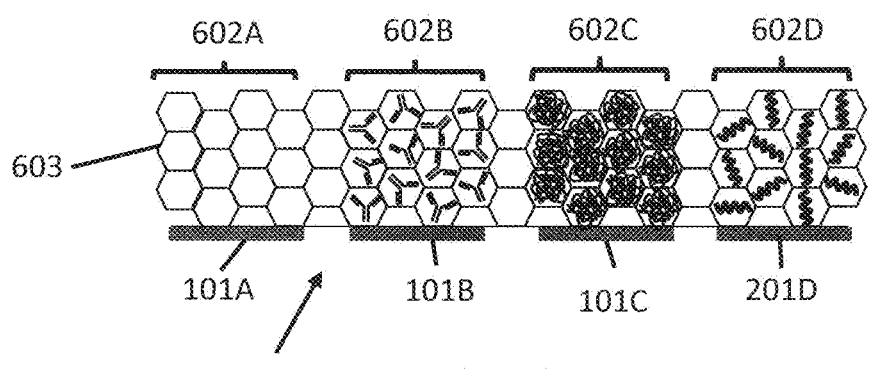
Figure 6C:
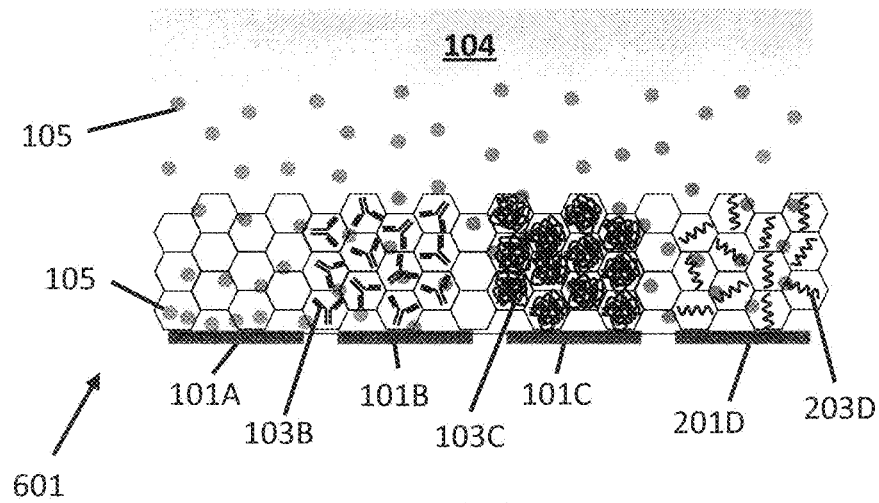

FIG. 6A-FIG. 6C is a schematic depiction of an embodiment of the invention in which multiple biomolecule binder types are coupled to a freestanding porous matrix, which is then registered to specific sensors in the array. In this aspect of the invention, binders are dispensed to freestanding porous matrix 601 that is not initially deposited on sensor array 102 (FIG. 6A). Methods and materials described above in the discussion of FIG. 5 for dispensing, dispersing, and coupling biomolecules to or for directly synthesizing biomolecule binders on deposited porous matrix 501 are also useful with freestanding porous support matrix 601 and structural segments 603. Similarly, the composition of freestanding porous matrix 601 and structural segments 603 may be any of those described above for 501 and 503. In some aspects of the invention, no binders are dispensed to freestanding porous matrix 601 over select sensor surfaces, as in region 602A of freestanding porous matrix 601.

As schematically depicted in FIG. 6B, freestanding porous matrix 601 comprising binders can be transferred to the surfaces of sensors 101A, 101B, 101C, 201D on sensor array 102. In some embodiments, freestanding porous matrix 601 is registered to sensor array 102 such that specific sensors 101 have selected specific binders 103. For example, region 602B of freestanding porous matrix 601 may receive antibody binders and be registered to sensor 101B. Similarly, region 602C may comprise peptides or protein binders with a specific conformation. Further, region 602D may comprise nucleic acid binders. Sensor array 102 can then be exposed to an interrogator gas sample, either before exposure to a test sample, as shown here in FIG. 6C or after exposure of the sensors to the test sample.

In some embodiments of the invention, binders comprising peptides 103C or nucleic acids 203D may be synthesized in situ on deposited porous support matrix 501 that is present on sensor array 102 or on freestanding porous support matrix 601. In certain aspects of the invention, synthesized peptides may comprise, at least 2, 3, 4, 5, 6, 7, 8, 9, 10, 15, 20, 25, 30, 35, 40, 45, 50, 60, 70, 80, 90, or 100 amino acids or any number therebetween and inclusive of the smaller and larger sizes listed. In other aspects of the invention, peptide length is not limited and may be any length that can be synthesized on a porous matrix 501 or 601 and that retains functionality as a binder for an analyte. Similarly, in certain aspects of the invention, synthesized nucleic acids may comprise, at least 2, 3, 4, 5, 6, 7, 8, 9, 10, 15, 20, 25, 30, 35, 40, 45, 50, 60, 70, 80, 90, or 100 nucleotides or any number therebetween and inclusive of the smaller and larger sizes listed. In other aspects of the invention, nucleic acid length is not limited and may be any length that can be synthesized on a porous matrix 501 or 601 and that retains functionality as a binder for an analyte. Representative methods for synthesizing peptides and nucleic acids on matrix surfaces can be found in Gao et al., (Proteomics, (2003) 3:2135-2141), and Gao et al., (U.S. Pat. No. 6,426,184).

In some embodiments of the invention, an analyte of interest is a chemical or chemical compound that is not a biomolecule. In other aspects of the invention, the chemical analyte is a biomolecule. As used herein in some aspects of the invention, "biomolecule" refers to a molecule that is produced or capable of being produced in or produced by a living organism. In additional aspects of the invention, a biomolecule is any molecule that is present in or on a living organism. In some embodiments of the invention, a biomolecule is an organic molecule. Exemplary organic biomolecules include proteins, peptides, polypeptides, oligopeptides, amino acids, polysaccharides, nucleic acids, DNA, and RNA. Additional exemplary biomolecules include small molecule metabolites, cytokines, hormones, lipids, antibodies, sugars, acids, bases, and other chemical compounds. In some aspects of the invention, biomolecules may be primary or secondary metabolites, aptamers, or receptors. In additional aspects of the invention, a biomolecule refers to an organic or inorganic degradation product of a biomolecule.

In some embodiments of the invention, a biomolecule analyte may be a cell, a pathogen, a virus, a prion, a fungus, a bacterium, or other organism or a part thereof that can be specifically recognized and sequestered or bound by a binder. In some aspects of the invention, a biomolecule analyte is a fragment of a cell or a cell structure, such as for example only, a region of a cell membrane, a fragment of a cell membrane, a liposome, or a cellular organelle such as a mitochondrion, a nucleus, a Golgi apparatus, or another subcellular structure. A biomolecule analyte may be on or in cell cytoplasm or a subcellular structure.

In additional embodiments of an invention, a biomolecule analyte or "bioanalyte" may be isolated from an organism. In some aspects of the invention, a biomolecule analyte may be purified or partially purified during or following isolation from an organism. Numerous methods for isolating and purifying biomolecules are known to those of skill in the art. It is also contemplated that novel purification methods not yet known in the art could be used for purifying biomolecules for use in embodiments of the invention. In addition, methods for in vitro synthesis of biological small molecules, antibodies, peptides, nucleic acids, cell membranes, membrane mimics, liposomes, and other biological structures are known in the art.

In certain aspects of the invention, analytes are extracted from solid, liquid or gaseous samples. Test and control samples may comprise gases, liquids, and chemical mixtures. A sample may be or may comprise, an extract of an environmental sample, such as for example an air sample or other gaseous sample, a liquid sample, or a soil extract or extract of a water sample. A water sample may contain an analyte that is a biological toxin or toxicant. In some aspects of the invention, test samples are prepared using methods designed to isolate or purify an analyte of interest in a form that will promote formation of an analyte-binder complex. Methods for extracting, isolating, or purifying biological molecules and chemicals from numerous types of samples, including biological, environmental and industrial or pharmaceutical manufacturing samples, are available in the art. In other aspects of the invention, a sample is not purified or extracted prior to contacting the sample with a gas sensor. In certain embodiments of the invention, analytes may be synthetically prepared in vitro. In some aspects of the invention a biomolecule analyte may be synthetically prepared in vitro and not isolated or purified from an organism, cell, or subcellular structure.

In some embodiments, a test sample or control sample comprises individual gases or liquids or mixtures of gases or liquids. In other embodiments, a test or control sample comprises a liquid having a corresponding vapor component.

In some embodiments of the invention, a biological test sample is from an organism. In additional embodiments, test samples are biological samples or extracts of biological samples. In some aspects of the invention, a biological test sample may be from or may comprise blood, serum, plasma, tissue, organs, semen, saliva, breath, tears, sputum, feces, urine, other bodily fluid, hair follicles, skin, or any sample containing or constituting biological cells. Biomolecule analytes for detection and quantification may be released from cell-bearing test samples after in situ cell lysis or be present extracellularly in a sample from a biological organism.

In some aspects of the invention, a biological sample is from a medical, pharmaceutical or biological manufacturing process. In one exemplary aspect of the invention, a sample can be a biological threat sample collected by military or first responders. In still other aspects of the invention, a biological test sample is from a patient. In some aspects of the invention, a sample is from a patient that has tested positive for a disease, a patient undergoing treatment, a patient with a tumor or known mutation that results in the production of a disease-specific analyte, or a patient suspected of having a disease or condition. A biological sample may also include one or more analytes indicative of the presence of a pathogen, a virus, a prion, a fungus, a bacterium, or another organism. In further embodiments, a sample may be collected by sampling ambient air around an object or a subject in order to detect an analyte indicative of a human or other organism or of recent human activity or other activity.

The presence and/or amount of one or more selected analytes in a test sample may be indicative of a disease or condition, may correlate with the severity of a disease or condition, may be used to evaluate the response of a patient to a treatment or may be used to optimize treatment of a patient. The presence or amount of an analyte in a biological sample may also be examined to evaluate and correlate the analyte with pharmacokinetics and to adjust the treatment of a patient such as with a compound or drug. In some aspects of the invention, an analyte may be a metabolic by-product or breakdown product of a treatment compound such as a drug.

In some aspects of the invention, a test or control sample comprises a synthetically prepared biological or chemical analyte. A synthetically prepared biological or chemical analyte may be a precursor or product of a biological, chemical or industrial manufacturing process. Synthetically prepared biomolecules, may be for example, synthetic nucleic acids or peptides. In specific aspects of the invention, synthetic analytes may be added to a test sample to serve as positive or negative controls for detection or as standards for quantification.

In another exemplary aspect of the invention, the presence and/or amount of an analyte in a test sample may be determined and evaluated for a patient tumor or blood sample prior to the patient being treated or during treatment to determine if there are analytes whose expression and/or concentration correlates with the outcome of the patient. Such determinations can lead to a diagnostic assay that can be used to evaluate tumor and/or blood samples to determine what drug regimen the patient should be provided. In addition, such determinations can be used to identify or select patients suitable for a particular clinical trial. The presence and/or amount of an analyte may be correlated with drug efficacy or drug toxicity that may be relevant to whether that patient is an appropriate patient for receiving the drug or for a particular dosage of the drug. In addition, biological samples from patients with a variety of diseases can be evaluated to determine if different diseases can be identified based on the presence or levels of selected one or more analytes. Some such correlations between biological analytes and specific diseases are known in the art.

Multiple analytes present in a single sample may be queried using methods of the invention. For example, selected individual gas sensors or groups of gas sensors may be derivatized with binders that form binder-analyte complexes with different selected analytes from a single sample. It is contemplated that many analytes can be queried at a single time, in a multiplexed assay format, by using arrays of multiple gas sensors that are derivatized with selected different binders.

The differences in control and test sample gas sensor response profiles observed with different gases can be used to increase sensitivity of analyte detection and to aid in quantification of an analyte in a test sample. Therefore, in some embodiments of the invention, evaluating a test sample for the presence of an analyte and for quantifying an analyte comprises two stages as illustrated in FIG. 7.

Figure 7:
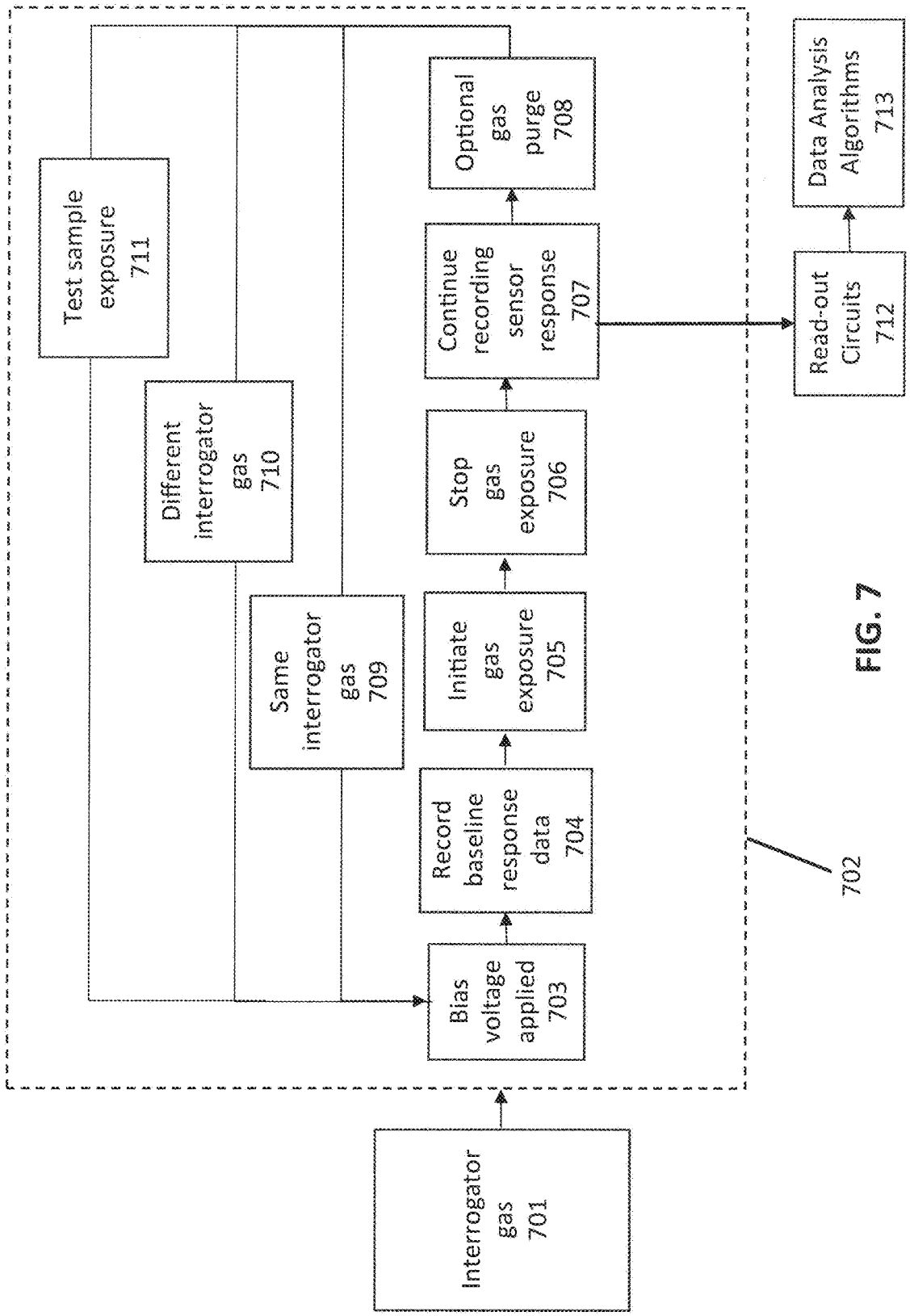
FIG. 7 is a flow chart of an exemplary workflow useful in some invention embodiments for analyzing a test sample to determine the presence or absence of an analyte and for quantifying an analyte in a test sample.

FIG. 7 is a flow chart of an exemplary workflow useful in some invention embodiments for analyzing a test sample to determine the presence or absence of an analyte and for quantifying an analyte in a test sample. In some embodiments of the invention, evaluating a test sample for the presence of an analyte comprises following a series of test and analysis protocols, testing regimen 702, as illustrated in FIG. 7. In these embodiments, analyte detection and analysis begins by determining a control gas sensor response profile (e.g., 107C) using interrogator gas 701 (e.g., 105) and a sensor (e.g., 101C) having binders (e.g., 103C) on the sensor surface. Determining a gas sensor response profile comprises steps 703 through 707 in FIG. 7 and begins by applying a bias voltage 703 across all sensors 101 in array 102. The bias voltage is applied for a sufficient duration to allow the sensors to stabilize to the environmental conditions (i.e., the sensors exhibit a relatively unchanging current value). After stabilization, determination of baseline response data 704 is initiated. After a selected period of time (typically a few seconds) of determining baseline data, gas exposure 705 is initiated and continues for a selected period of time prior to stopping the gas exposure 706. Exposure times may range from a few milliseconds to hundreds or even thousands of seconds. It is specifically contemplated that gas sample exposure times may be for any selected length of time in that range. Sensor response profile data are determined from the selected baseline time point, throughout gas exposure, and after the gas exposure period 707 to the selected end time point. Data determination periods can range from seconds to hours. In some embodiments of the invention, it is specifically contemplated that there is no limit on the time period for data determination. An optional gas sample purge step 708, such as pulsing clean dry air over the sensors with or without heating, may be employed to clear gas from the sensors, prior to repeating the process with either the same interrogator gas 709 (e.g., 105) or with a different interrogator gas 710 (e.g., 305).

After determining a control sensor response profile with interrogator gas 701, sensors 101 on array 102 are exposed to test sample 711 which may comprise one or more analytes of interest in a variety of concentrations. After exposure of sensors 101 to test sample 711 under appropriate conditions and termination of test sample exposure, test sample sensor response profiles (e.g., 110C) are determined using a separate sample of interrogator gas 701 (e.g., 105) and sensors (e.g., 101C) having any binder-analyte complexes (e.g., 109C) that may have formed during incubation with test sample 711. In aspects of the invention, a control sensor response profile is typically performed using the same sensor that will be used for analyzing the test sample; however, the control sensor response profile is determined prior to exposure of the sensor to a test sample 711. As for determination of control sensor response profiles described above, an optional gas sample purge step 708, such as pulsing clean, dry air over the sensors with or without heating, may be employed to clear gas from the sensors, prior to repeating the process with test sample 711 and either the same interrogator gas 709 or with a different interrogator gas 710.

In some aspects of the invention, determining baseline and other sensor response data (i.e., determining a gas sensor response profile) comprises recording the data. In other aspects of the invention, sensor response data are plotted graphically. In still further aspects of the invention, sensor response data are analyzed by read out integrated circuits (ROIC) 712 and may be further analyzed with data analysis algorithms 713.

In certain embodiments of the invention, a plurality of gas sensor response profiles are determined for exposure of a sensor to the same interrogator gas sample 709 and may be employed in testing regimen 702. In additional embodiments, one or more determinations of gas sensor response profiles for exposure of a sensor to a different interrogator gas sample 710 may be employed in testing regimen 702. There is no limit to the number of replicates of testing regimen 702 that may be performed with the same 709 or different 710 interrogator gases.

In various embodiments of the invention, the duration of gas exposure may be varied. By way of example only, gas exposure duration times may be about 0.001 sec, 0.01 sec, 0.1 sec, 0.2 sec, 0.5 sec, 1 sec, 2 sec, 5 sec, 10 sec, 20 sec, 30 sec, 60 sec, 120 sec, 300 sec, 400 sec, 500 sec, 1,000 sec or any specific selected duration between about 0.001 sec and about 1,000 sec or more inclusive. Any gas exposure duration time may be used in combination with any number of replicates performed with the same or different gases.

In some embodiments of the invention, gas sensor response profiles can be determined at the same time for all gas sensors that are present in array 102, using ROICs 712, such as for example, ROICs comprising silicon CMOS logic. Determination of sensor response profiles provides data for use with analysis algorithms 713 to enable analyte identification and quantification.

In some embodiments of the invention, control sensor response profiles are determined using various types and configurations of binders and/or gas sensors. One or more control sensor response profiles and test sample sensor response profiles may be stored in a database, and comparing sensor response profiles comprises comparing one or more test sample response profiles to one or more control response profiles stored in the database. Comparisons of these stored gas sensor response profiles can be used to determine the identity and concentration of one or more analyte in a test sample. In additional aspects of the invention, deconvolution of gas sensor response data enables the identification and quantification of analytes in a test sample.

Qualitative and quantitative differences between the control sensor response profiles (determined with interrogator gas 701 prior to exposure of gas sensors to test sample 711) and the test sample gas sensor response profiles (determined with interrogator gas 701 after exposure of gas sensors to test sample 711) are identified for each sensor employed. Qualitative and quantitative differences and similarities among control sample sensor response profiles and test sample sensor response profiles can be determined by using ROIC 712 and data analysis algorithms 713 and comparing data from control sensor response profiles with data from test sample sensor response profiles. Numerous computational algorithms are available in the art that are useful for identifying differences in datasets. Such algorithms are applicable for determination of qualitative and quantitative differences between sensor response profiles. In general, quantification of an analyte in a test sample is made by determining the maximum change in sensor response between a control sensor response profile and a test sample sensor response profile determined with the same interrogator gas 709. Quantification of an analyte can be enhanced by comparing control and test sample sensor response profiles determined using additional different interrogator gases 710 and by cross comparison of sensor response profile data from all sensors in a sensor array 102 acquired for each different interrogator gas species 710 using testing regimen 702.

The inventors observed that, upon exposing underivatized sensors (i.e., bare sensors without binders, linkers, a porous matrix, or other molecules, (e.g., 101A as in FIG. 1) to interrogator gas comprising purified gases using testing regimen 702, the determined gas sensor response profiles were different for each gas. For use in some embodiments of the invention, derivatized sensors lacking binders may comprise linkers 401.

FIG. 8 shows multiple gas sensor response profiles determined for each of six different volatile organic compound gases and for water, using a sensor derivatized with linker structures only (no binder derivatization). For this experiment, the inventors used arrays of conductometric semiconducting tin oxide ($SnO_x$) nanotrace sensors, each nanotrace being 80 nm in width, prepared using nanoimprint lithography according to methods described in Savoy et al., U.S. Pat. No. 8,450,131. Gas sensor response profiles were determined for each of six different exemplary interrogator volatile organic compound (VOC) gases and for water 802, according to testing regimen 702. The volatile organic compound (VOC) gases included 4-methylbenzaldehyde 801, 4-methyl valeric acid 803, benzaldehyde 804, 2,4-dimethyl acetophenone 805, 2-ethyl hexanoic acid 806, and 2-ethylhexanol 807. Sensor response profiles for each gas were determined using 64 independently addressable nanotrace sensors (56 sample sensors shown in FIG. 8 and 8 blank control sensors having no semiconducting metal oxide that are not shown in the figure).

Gas sensor response profiles were determined according to methods described above (FIG. 7), by measuring the electrical current flowing through the sensor as a function of time, beginning at a selected time point prior to initiation of gas exposure and continuing through the length of the gas exposure and for a selected period of time after exposure of the sensor to the gas was stopped. Bias voltage was applied and the average value of baseline current 810 was measured in the 5 sec period prior to initiation of gas exposure. Underivatized sensors were exposed to a gas sample at time (t)=0 sec (represented as dashed line 808). Gas exposure was stopped at t=15 sec (represented as dashed line 809).

Gas sensor response data (i.e., current measurements) were converted to normalized resistance over time using Ohm's law (V=IR) and the applied bias, typically between 0.01 to 12 V. In this example, each gas sensor response profile, plotted as normalized resistance vs. time, was normalized by dividing the value of all data points on the gas sensor response profile with the average value of the baseline current 810. For the seven sets of 56 gas sensor response profiles for each gas in FIG. 8, current measurements were aligned at t=0 sec.

The inventors found that multiple determinations of gas sensor response profiles, using the same gas species exhibited the same pattern (FIG. 8), and gas sensor response profiles differed among water and the different gas species. The sensor response profiles for water and each gas species 801-807 exhibited differences in the rate of sensor response rise, the maximum change in sensor response, and the rate of response fall after stopping gas exposure. These characteristics of the sensor response profiles indicate different responses to each gas. The gas sensor response profile represents a composite effect resulting from the sample gas diffusion rate, the rate of adsorption of the gas onto the sensor, the rate of desorption of the gas from the sensor, and the effect on charge carrier mobility and carrier concentration of the sensor when gas molecules are adsorbed on the sensor surface. In some aspects of the invention, exposure of a gas sensor to certain gas species may result in no sensor response changes, such as when a gas sensor is exposed to clean dry air. In these aspects, the response remains unchanged until sample exposure to sensor 101A is stopped 809. The presence of binder 103 on the sensor surface may further impact the sensor response profile, and ultimately, the formation of analyte-binder complexes during test sample exposure will alter the subsequently-determined sensor response profile even further, such that specific differences among control and test sample response profiles may be attributed to the presence of a specific analyte in a test sample.

Sensor response profiles may also be sensitive to temperature or relative humidity. In some aspects of the invention, test sample and control response profiles may be determined at a temperature that is approximately room temperature (~25 C) or at a temperature that is above or below room temperature. In some aspects of the invention, test sample and control response profiles may be determined at a relative humidity that is approximately (~50%) or at a relative humidity that is above or below ~50%.

Figure 9A:
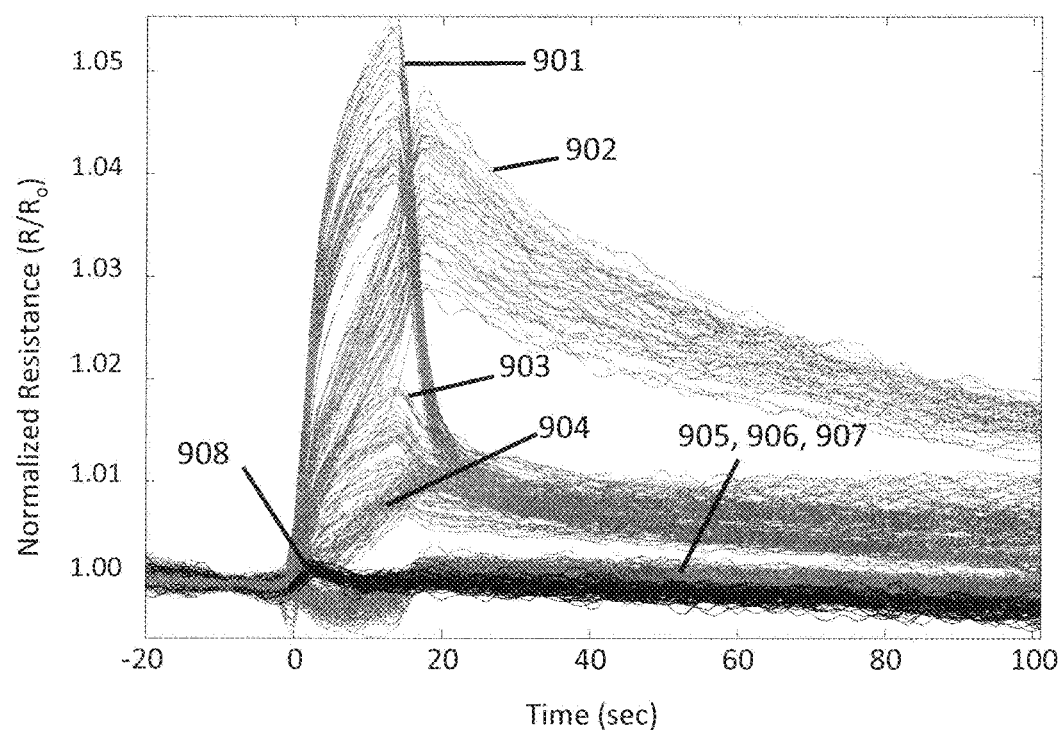
FIG. 9A-FIG. 9D.
Figure 9B:
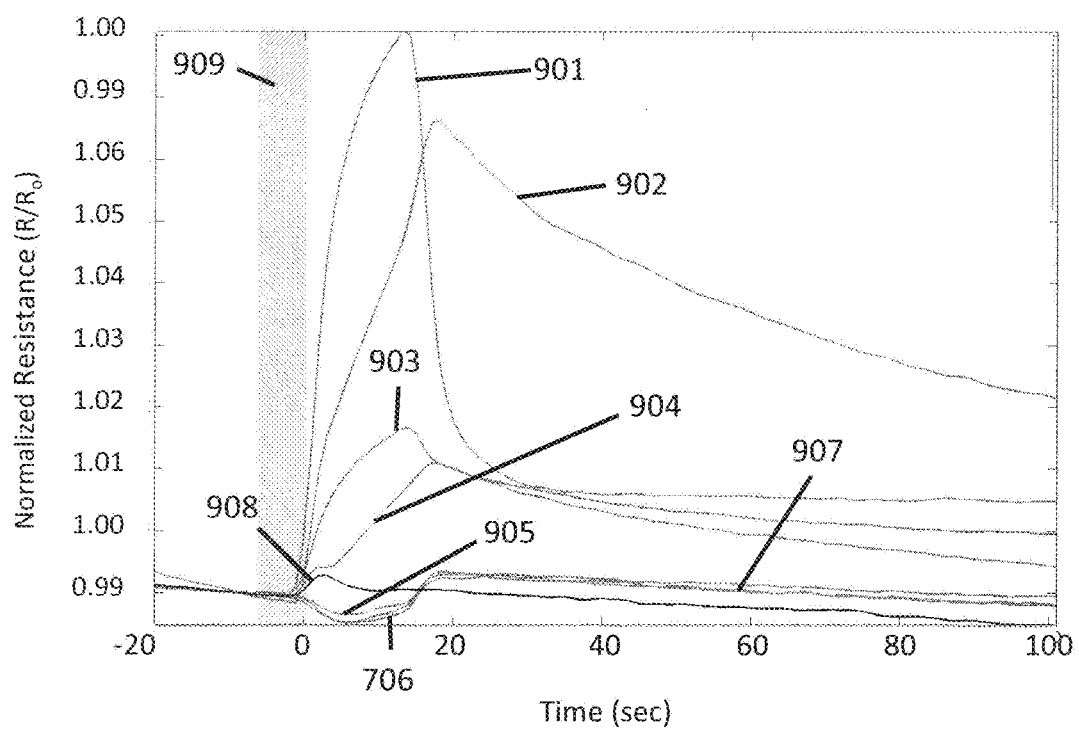
Figure 9C:
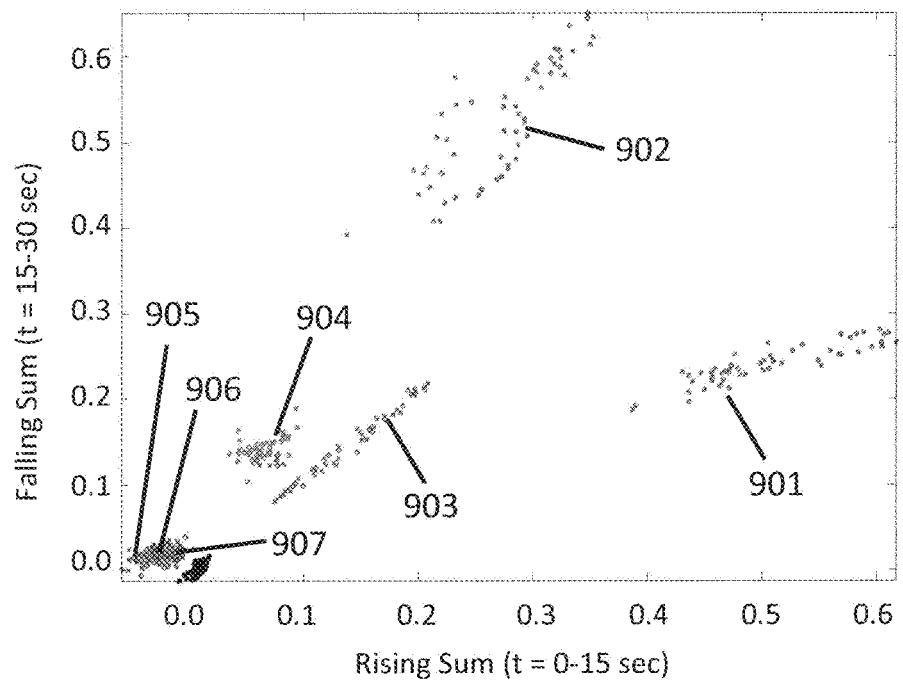
Figure 9D:
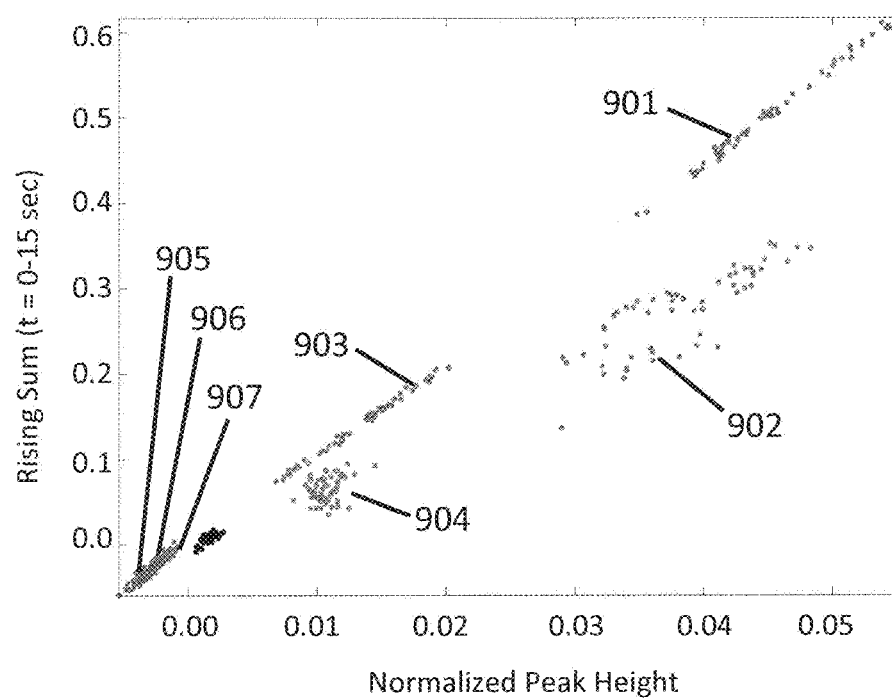

FIG. 9A-FIG. 9D. FIG. 9A shows multiple gas sensor response profiles determined using a sensor derivatized with linker structures, for each of seven different exemplary interrogator volatile organic gases from common industrial solvents. FIG. 9B shows the averaged gas sensor response profile from all sensors for each interrogator gas. FIG. 9C and FIG. 9D show principal component analysis plots using data from the gas sensor response profiles. Gas sensor response profiles with similar characteristics were observed for multiple replicates of volatile organic compound gas samples such as common industrial solvents. Fifty-six (56) gas sensor response profiles determined for each sample gas are shown in FIG. 7A. The gases were methanol 901, diethylether 902, dichloromethane 903, acetone 904, hexanes 905, toluene 906, and xylene 907. Similar to the response profiles shown in FIG. 8, the sensor response profiles for each gas type 901-907 exhibited differences in the rate of sensor response rise, the maximum change in sensor response, and the rate of sensor response fall after stopping gas exposure. These differences are more clearly apparent when the averaged gas sensor response profiles from all sensors for each gas are plotted (FIG. 9B). Switching noise may cause a false response such as that observed for sensor response profile 908, which was determined for clean dry air. Switching noise from the gate value and other electronic interference artifacts can be removed by shielding. Sensor response profiles 901-908 were normalized to data collected during the time range just before gas exposure as illustrated by the shaded area 909 of FIG. 9B.

In this example, gas sensor response profiles were determined for all 56 sensors for each gas (FIG. 9A). Sensor response profiles differed among the gases. However, the response profile for each sensor in the array was found to be highly reproducible among the 56 replicate measurements for each gas. Replicate sensors showed high precision (S.D.<2%). Principal component comparison plots of the falling sum vs. the rising sum (FIG. 9C) and the rising sum vs. the normalized peak height (FIG. 9D) show the differences in the response profiles among the individual responses. In addition, the plots illustrate that sample gases with similar chemical functional groups such as nonpolar aliphatic and aromatic hydrocarbons 905, 906, 907 behave similarly and display the least differences in the respective response profiles. In embodiments of the invention, improved separation of these gas species can be achieved by derivatizing sensor surfaces with different binders. Ultimately, primary differences between gas sensor response profiles for sensors with binder only, and for sensors with binder-analyte complexes on sensor array 102 can be used to identify and quantify target analytes.

To determine the gas sensor response profiles illustrated in FIG. 8 and FIG. 9, a sample of solvent vapor at the full vapor pressure at room temperature was isolated in an impinger vessel or directly connected from a lecture bottle of the gas. Gas exposure was accomplished by directing a fixed flow rate of a carrier gas (measured as sccm) into the liquid impinger using a mass flow controller. Examples of carrier gases include dry air, argon, or other inert gases. This sample stream was recombined with the stream of carrier gas then directed over the gas sensor for fixed time intervals ranging from 1 sec-300 sec. The concentration of the control gas is controlled using mass flow controllers. In other embodiments of the invention, control gas can be diluted with or directly combined into a background carrier gas that is directed over the surface of gas sensor 101.

In some experiments, responses were determined for each sensor as the ratio ($R_s/R_0$) converted from the measured sample current ($I_s$) using the applied bias voltage V and Ohm's law and a normalization procedure. Current measurements were first determined at a fixed voltage, typically in the range of 0.1V-1V. Useful fixed voltages may be as low as 1 microVolt to as high as hundreds of Volts. In additional embodiments of the invention, normalization involves dividing each calculated resistance value of the response ($R_s$) with the measured resistance just prior to sample exposure ($R_0$).

Figure 10A:
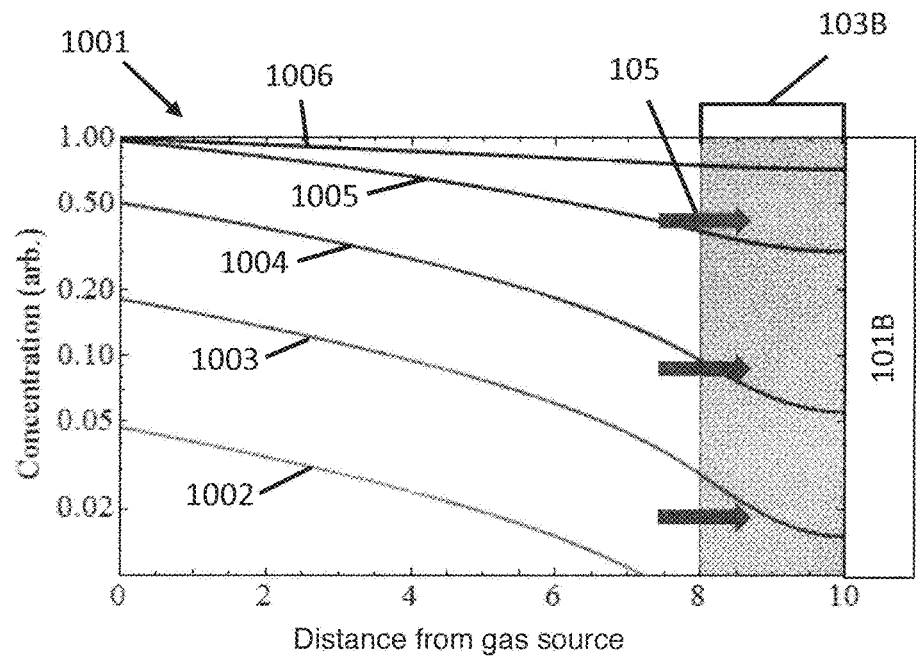
FIG. 10A-FIG. 10C.
Figure 10B:
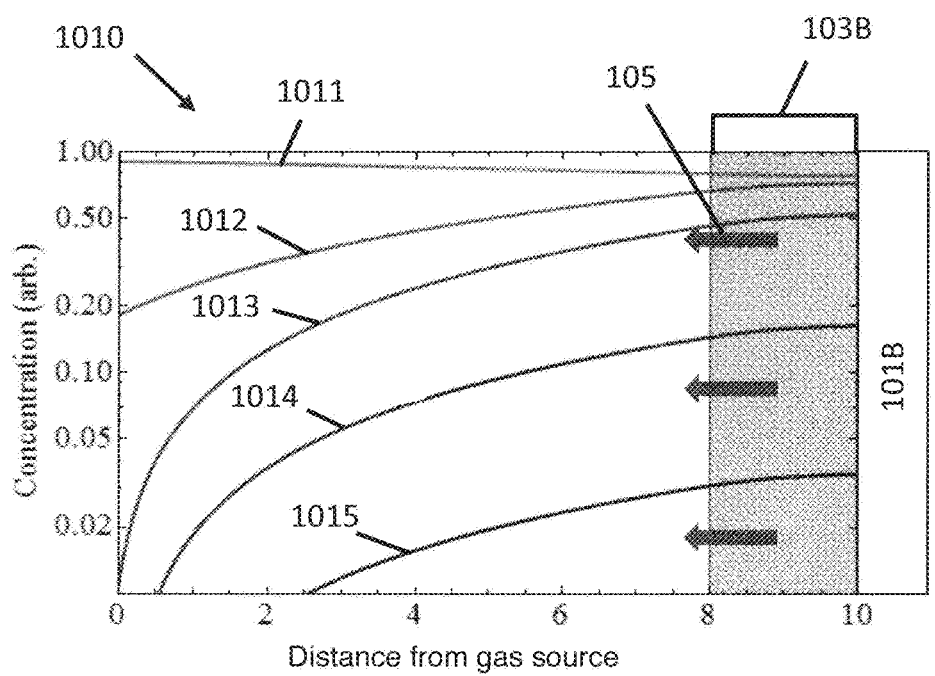
Figure 10C:
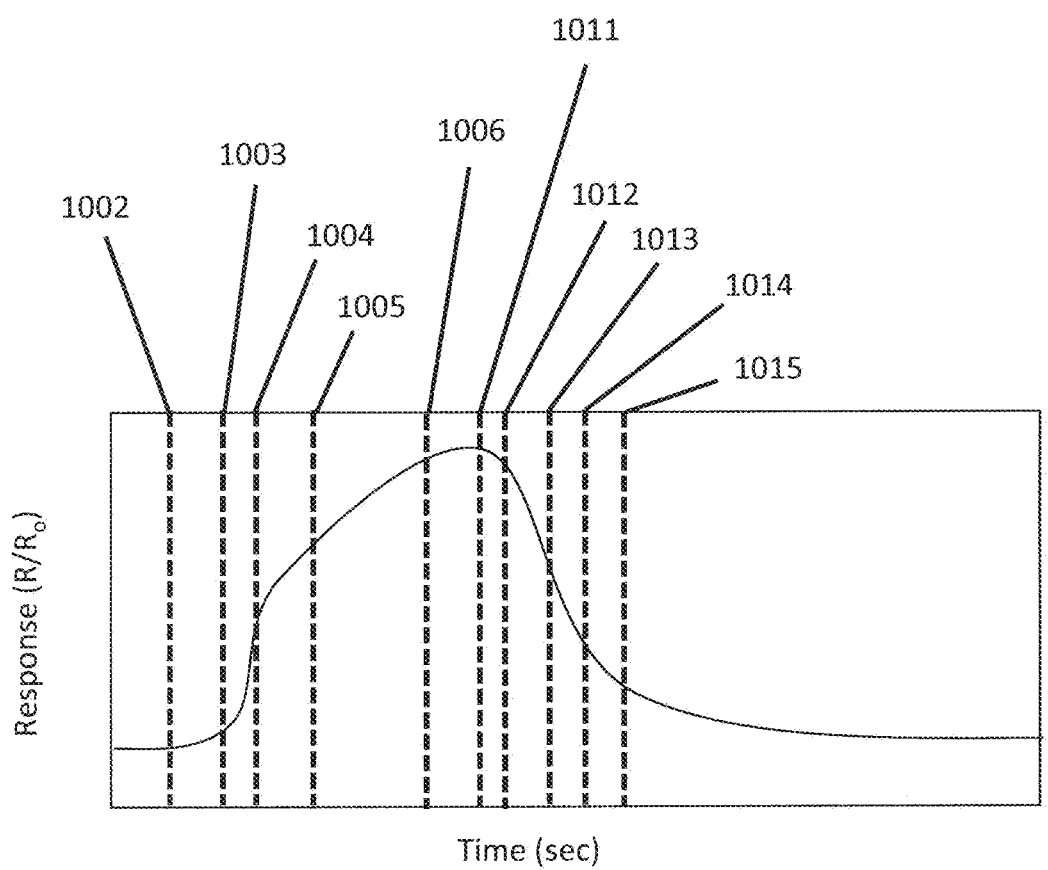

FIG. 10A-FIG. 10C. FIG. 10A and FIG. 10B illustrate concentration profile curves representing the concentration distribution of a gas between a gas source and a sensor derivatized with a binder, during gas exposure and diffusion of an exemplary interrogator gas to the sensor (FIG. 10A) and after stopping gas exposure and during diffusion of interrogator gas from the sensor (FIG. 10B). FIG. 10C shows the corresponding gas sensor response profile and the position in time corresponding to each concentration profile curve. In FIG. 10A and FIG. 10B, for ease of viewing, binders are shown as shaded rectangles, and the gas is represented as horizontal arrows. Concentration (arb.) (y-axis) refers to concentration represented as arbitrary units. Distances from gas source (x-axis) are in arbitrary units.

FIG. 10A is a one-dimensional concentration profile simulation 1001 for interrogator gas 105, at different times during gas exposure and diffusion of gas to the sensor. Concentrations are expressed as the log concentration of the gas in arbitrary units (arb.) (y-axis) as a function of the distance from gas source in arbitrary units (x-axis). In FIG. 10A, each concentration profile curve (1002, 1003, 1004, 1005, 1006) represents the gas concentration at positions between the gas source and sensor 101B at a specific time during gas exposure when gas molecules are diffusing through binders 103B and becoming adsorbed to the surface of gas sensor 101B. An exemplary, sample exposure duration may be 30 sec, and the concentration profile curves 1002-1006 may represent gas concentration profiles determined at, for example, 1 sec, 5 sec, 10 sec, 15 sec, and 30 sec, respectively, following initiation of gas exposure. Gas concentration at the sensor surface increases with increasing time of gas exposure, e.g., curve 1006 representing the longest time after initiation of gas exposure. The simulation is primarily based on Fick's diffusion law, treating the binder only with a diffusion coefficient distinct from the region between the outermost surface of the binder 103B on sensor 101B and the gas source (at position 0 on the x-axis). The simulation takes into account diffusion parameters and the adsorption and desorption rates of the gas molecules on the surface of the sensor.

FIG. 10B shows a one-dimensional concentration profile simulation 1010 for interrogator gas 105, at specific times after gas exposure is stopped, expressed as the log concentration of the gas in arbitrary units (arb.) (y-axis) as a function of the distance from gas source (x-axis). In this period, the gas flowing over sensor 101B comprises only carrier gas, not interrogator gas. As such, some gas molecules desorb from the surface of gas sensor 101B and diffuse away, with carrier gas, from the sensor through binders 103B. The concentration profile curves 1011, 1012, 1013, 1014, and 1015 represent gas concentrations at progressively longer times, at positions between the gas source and the outermost surface of binders 103B, after gas exposure is stopped. Gas concentration at the surface of sensor 101B is highest at the shortest time point after interrogator gas exposure has stopped, represented by curve 1011, and is lowest at the longest time point after interrogator gas exposure has stopped, represented by curve 1015.

FIG. 10C shows the corresponding gas sensor response profile and the position in time corresponding to each concentration profile curve 1002, 1003, 1004, 1005, 1006, 1011, 1012, 1013, 1014, and 1015 shown in FIGS. 10A and 10B. The intersection of a concentration profile curve with the gas sensor response profile curve correlates the amount of interrogator gas adsorbed on sensor 101B with the sensor response at that time, during diffusion of gas to the sensor (FIG. 10A, 1002-1006) and during diffusion of gas away from the sensor (FIG. 10B, 1011-1015). Sensor response is greatest at the time interval between 1006 and 1011 when the concentration of interrogation gas at the sensor surface is near saturation (i.e., the maximum number of sensor surface sites are occupied by interrogator gas 105).

Figure 11A:
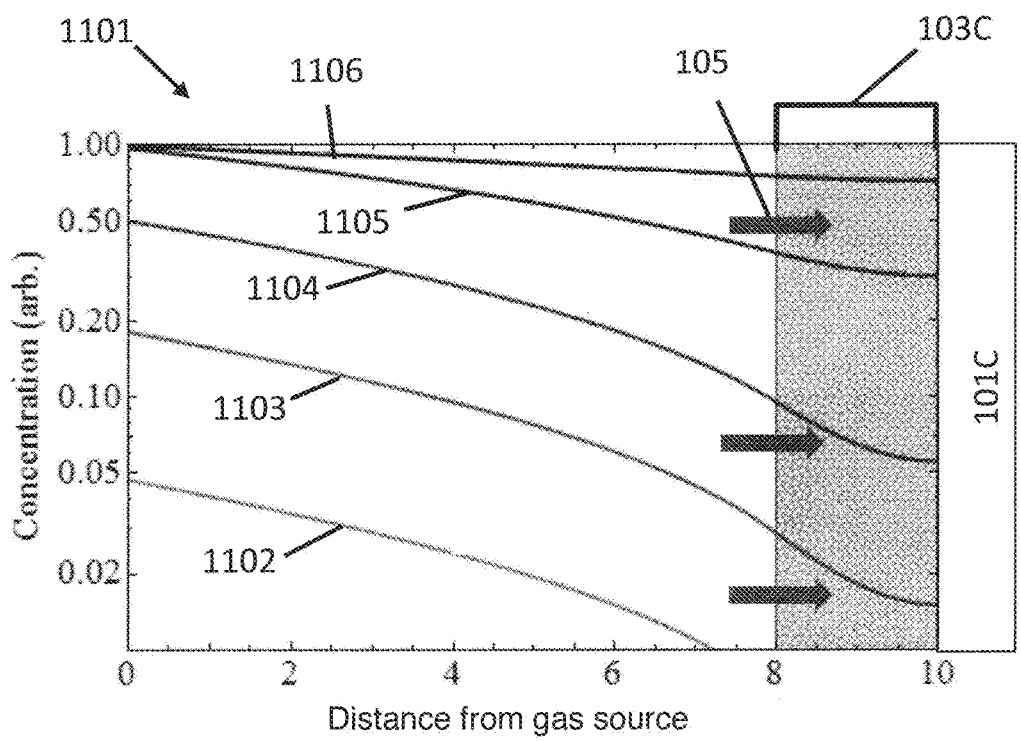
FIG. 11A-FIG. 11D. illustrate concentration profile curve simulations representing the concentration distribution of a gas between a gas source and a sensor during gas exposure and diffusion of gas to the sensor and after stopping gas exposure and during diffusion of gas from the sensor.
Figure 11B:
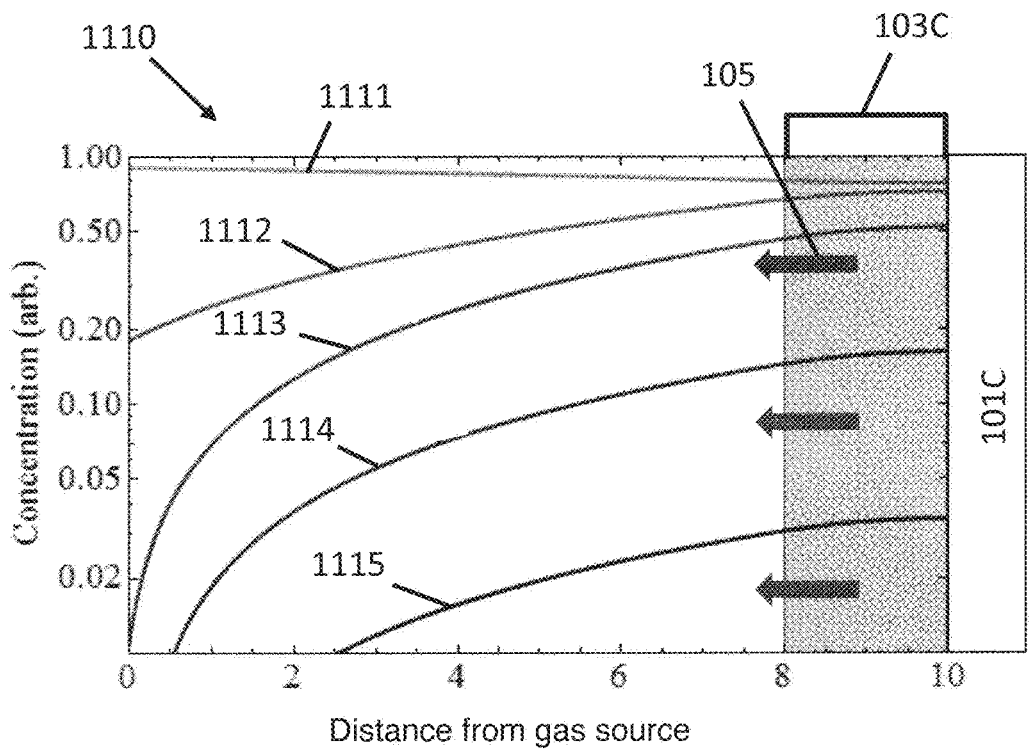
Figure 11C:
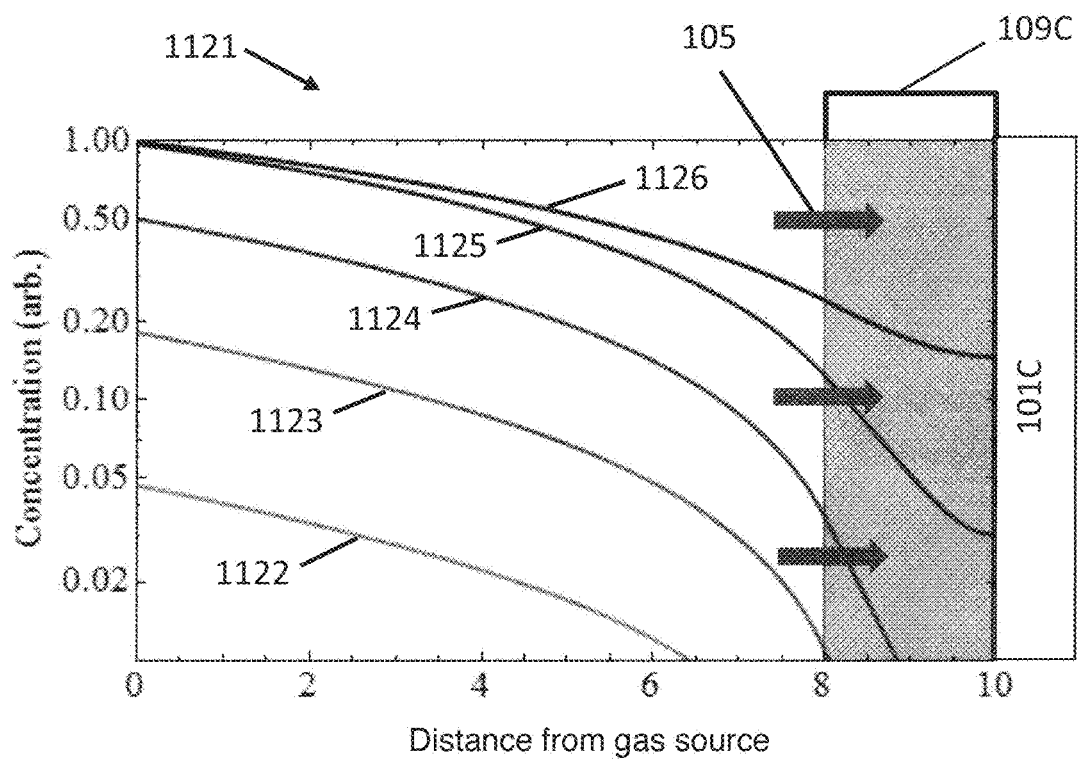
Figure 11D:
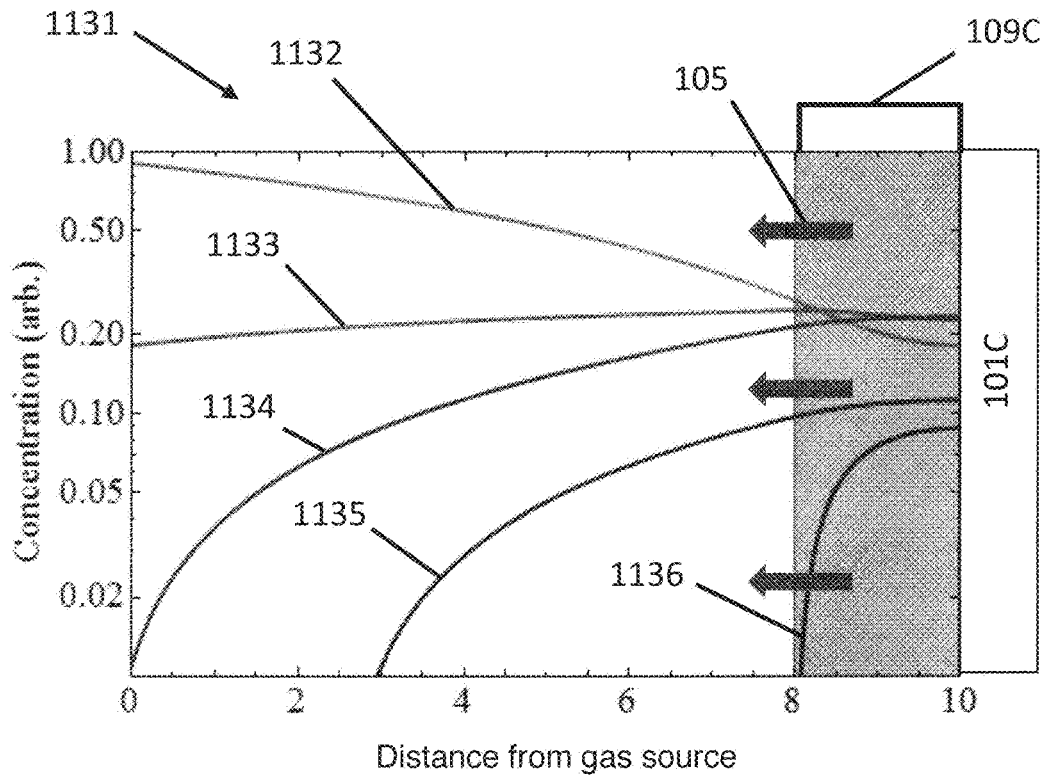

FIG. 11A-FIG. 11D illustrate concentration profile curve simulations representing the concentration distribution of a gas between a gas source and a sensor during gas exposure and diffusion of gas to the sensor and after stopping gas exposure and during diffusion of gas from the sensor. FIG. 11A and FIG. 11B are simulations for a sensor having a binder. FIG. 11C and FIG. 11D are simulations for a sensor having a binder-analyte complex. For ease of viewing, the binder and binder analyte complexes are shown as shaded rectangles and the gas is represented as horizontal arrows. Concentration (arb.) refers to concentration represented as arbitrary units. Distances from gas source (x-axis) are in arbitrary units.

FIG. 11A and FIG. 11B show the one-dimensional concentration profile simulations for the embodiment in which binder 103C is anchored on the sensor surface 101C representing concentration profile curves (1102, 1103, 1104, 1105, 1106) during an interrogator gas exposure (1101) and concentration profile curves (1111, 1112, 1113, 1114, 1115) after gas exposure has been stopped (1110). In contrast, FIG. 11C-FIG. 11D show the one-dimensional concentration profile simulations for the embodiment in which contact with a test sample having an analyte results in the formation of binder-analyte complexes 109C on sensors 101C representing concentration profile curves (1122, 1123, 1124, 1125, 1126) during gas exposure (1121) and concentration profile curves (1132, 1133, 1134, 1135, 1136) after gas exposure has been stopped (1131). The diffusion of interrogator gas through analyte-binder complexes 109C is different than the diffusion of interrogator gas through only binders 103C, as can be seen when concentration profile curves 1122-1126 are compared to concentration profile curves 1102-1106 (concentrations during gas exposure) and when concentration profile curves 1132-1136 are compared to concentration profile curves 1111-1115 (concentrations after gas exposure has been stopped). In embodiments of the invention, the resulting differences in a gas sensor response profile determined for gas flowing through binders 103C alone and the gas sensor response profile determined for gas flowing through analyte-binder complexes 109C (after exposure to a test sample) can be used to determine the presence of and quantify the amount of an analyte in a test sample.

What is claimed is:

1. A method of determining the presence of an analyte in a test sample, the method comprising the steps of:
    (a) exposing a gas sensor, derivatized with analyte binders capable of interacting specifically with the analyte, to a first gas sample comprising a known interrogator gas species and lacking the analyte;
(b) stopping sensor exposure to the first gas sample;
(c) determining a first gas sensor response profile from a selected time prior to initiating sensor exposure to the first gas sample to a selected time after stopping sensor exposure to the first gas sample and during diffusion of the known interrogator gas species to and from the sensor and through the analyte binders;
(d) exposing the sensor to the test sample, under conditions effective for formation of binder-analyte complexes;
(e) terminating exposure of the sensor to the test sample;
(f) after terminating exposure of the sensor to the test sample,
  i) exposing the sensor to a second gas sample, the second gas sample comprising the known interrogator gas species,
  ii) stopping sensor exposure to the second gas sample, and
  iii) determining a second gas sensor response profile from a selected time prior to initiating sensor exposure to the second gas sample to a selected time after stopping sensor exposure to the second gas sample and during diffusion of the known interrogator gas to and from the sensor; and
(g) indicating a presence of the analyte in the test sample if the first and second gas sensor response profiles indicate that diffusion of the known interrogator gas species to and from the sensor and through the analyte binders is different from diffusion of the known interrogator gas species to and from the sensor after terminating exposure of the gas sensor to the test sample.

2. The method of claim 1 wherein the first and second gas samples each comprise a plurality of known interrogator gas species and wherein the known interrogator gas species are the same in the first and second gas samples.

3. The method of claim 1 further comprising comparing the first and second gas sensor response profiles by performing a ratiometric comparison of the profiles.

4. The method of claim 1 wherein the analyte binders are biomolecules.

5. The method of claim 1 wherein the analyte is a biomolecule.

6. The method of claim 5 wherein the test sample comprises a biological sample.

7. The method of claim 1 wherein the gas sensor is in a sensor array.

8. The method of claim 1 wherein the gas sensor is a conductometric semiconducting metal oxide sensor.

9. The method of claim 8 wherein the gas sensor comprises a plurality of nanotraces made by nanoimprint lithography.

10. The method of claim 9 wherein two or more nanotraces have different widths.

11. The method of claim 1 wherein the analyte binders are attached to the gas sensor with linkers.

12. The method of claim 1 wherein the analyte binders are coupled to a porous matrix.

13. The method of claim 1 further comprising quantifying the analyte.

14. A method of detecting the presence of a plurality of different selected analytes in a test sample, the method comprising:
(a) exposing at least a first gas sensor and a second gas sensor to a first gas sample comprising a known interrogator gas species and lacking at least a first analyte and a second analyte, wherein the first gas sensor is derivatized with selected first analyte binders capable of interacting specifically with the first analyte and the second gas sensor is derivatized with selected second analyte binders capable of interacting specifically with the second analyte;
(b) stopping exposure of the first and second gas sensors to the first gas sample;
(c) determining a first gas sensor response profile from a selected time prior to initiating exposure of the first gas sensor to the first gas sample to a selected time after stopping exposure of the first gas sensor to the first gas sample and during diffusion of the known interrogator gas species to and from the first gas sensor and through the selected first analyte binders;
(d) determining a second gas sensor response profile from a selected time prior to initiating exposure of the second gas sensor to the first gas sample to a selected time after stopping exposure of the second gas sensor to the first gas sample and during diffusion of the known interrogator gas species to and from the second gas sensor and through the selected second analyte binders;
(e) exposing the first gas sensor to the test sample under conditions effective for formation of first binder-analyte complexes comprising the first analyte and the selected first analyte binders and, exposing the second gas sensor to the test sample under conditions effective for formation of second binder-analyte complexes comprising the second analyte and the selected second analyte binders;
(f) terminating exposure of the first and second gas sensors to the test sample;
(g) after terminating exposure of the first and second gas sensors to the test sample,
  i) exposing the first and second gas sensors to a second gas sample, the second gas sample comprising the known interrogator gas species,
  ii) stopping exposure of the first and second gas sensors to the second gas sample,
  iii) determining a third gas sensor response profile from a selected time prior to initiating exposure of the first gas sensor to the second gas sample to a selected time after stopping exposure of the first gas sensor to the second gas sample and during diffusion of the known interrogator gas species to and from the first gas sensor; and
  iv) determining a fourth gas sensor response profile from a selected time prior to initiating exposure of the second gas sensor to the second gas sample to a selected time after stopping exposure of the second gas sensor to the second gas sample and during diffusion of the known interrogator gas to and from the second gas sensor;
(h) indicating a presence of the first analyte in the test sample if the first and third gas sensor response profiles indicate that diffusion of the known interrogator gas species to and from the first gas sensor and through the selected first analyte binders is different from diffusion of the known interrogator gas species to and from the first gas sensor after terminating exposure of the first gas sensor to the test sample; and
(i) indicating a presence of the second analyte in the test sample if the second and fourth gas sensor response profiles indicate that diffusion of the known interrogator gas species to and from the second gas sensor and through the selected second analyte binders is different from diffusion of the known interrogator gas species to and from the second gas sensor after terminating exposure of the second gas sensor to the test sample.

15. The method of claim 14 wherein the first, second, third, and fourth gas sensor response profiles are stored in a database.

16. The method of claim 15 further comprising determining the quantities of the at least first and second analytes in the test sample.

17. The method of claim 15 further comprising comparing the first and third gas sensor response profiles and comparing the second and fourth gas sensor response profiles using read-out integrated circuits and implementing data analysis deconvolution algorithms.

* * * * *